(12) United States Patent
Granvold et al.

(10) Patent No.: US 12,057,205 B2
(45) Date of Patent: Aug. 6, 2024

(54) GENERATION OF CUSTOMIZED PERSONAL HEALTH ONTOLOGIES

(71) Applicant: Apple Inc., Cupertino, CA (US)

(72) Inventors: Patrick W. Granvold, Oakland, CA (US); Jason B. Morley, San Francisco, CA (US); Zhe Li, Santa Monica, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/235,105

(22) Filed: Aug. 17, 2023

(65) Prior Publication Data

US 2023/0402139 A1    Dec. 14, 2023

Related U.S. Application Data

(63) Continuation of application No. 18/105,142, filed on Feb. 2, 2023, now Pat. No. 11,823,780, which is a continuation of application No. 17/883,916, filed on Aug. 9, 2022, now Pat. No. 11,636,931, which is a
(Continued)

(51) Int. Cl.
| | |
|---|---|
| *G16H 10/60* | (2018.01) |
| *G16H 40/20* | (2018.01) |
| *G16H 40/63* | (2018.01) |
| *G16H 40/67* | (2018.01) |
| *G16H 50/30* | (2018.01) |
| *G16H 50/70* | (2018.01) |

(52) U.S. Cl.
CPC ............. *G16H 10/60* (2018.01); *G16H 40/20* (2018.01); *G16H 40/63* (2018.01); *G16H 40/67* (2018.01); *G16H 50/30* (2018.01); *G16H 50/70* (2018.01)

(58) Field of Classification Search
CPC ........ G16H 10/60; G16H 40/67; G16H 40/63; G16H 50/30
USPC .......................................................... 700/90
See application file for complete search history.

(56) References Cited

U.S. PATENT DOCUMENTS

| | | | |
|---|---|---|---|
| 10,628,553 B1 | 4/2020 | Murrish et al. | |
| 11,475,984 B2 | 10/2022 | Granvold et al. | |
| 11,636,931 B2 | 4/2023 | Granvold et al. | |

(Continued)

FOREIGN PATENT DOCUMENTS

| | | |
|---|---|---|
| CN | 104718550 A | 6/2015 |
| CN | 105740307 A | 7/2016 |

(Continued)

OTHER PUBLICATIONS

US 11,783,926 B2, 10/2023, Granvold et al. (withdrawn)

(Continued)

*Primary Examiner* — Ted M Wang
(74) *Attorney, Agent, or Firm* — Kilpatrick Townsend & Stockton LLP

(57) ABSTRACT

A user interface may be used to present a graph that represents observable values from health record data stored on a user device. A personal health ontology stored on the user device may be accessed. At least one observable value of the observable values may be determined to be of a type of data for which a filter exists by at least accessing the personal health ontology. A filter may be added to the least one observable value. The user interface including the graph may be presented and the filter may be applied to the at least one observable value.

20 Claims, 27 Drawing Sheets

Related U.S. Application Data continuation of application No. 16/888,556, filed on May 29, 2020, now Pat. No. 11,475,984.

(60) Provisional application No. 62/855,953, filed on Jun. 1, 2019.

(56) References Cited

U.S. PATENT DOCUMENTS

| | | |
|---|---|---|
| 2011/0099280 A1 | 4/2011 | Thomas et al. |
| 2011/0161110 A1 | 6/2011 | Mault |
| 2011/0213869 A1 | 9/2011 | Korsunsky et al. |
| 2013/0096946 A1 | 4/2013 | Shah et al. |
| 2014/0136233 A1* | 5/2014 | Atkinson ............... G16H 15/00 705/3 |
| 2014/0200916 A1 | 7/2014 | Chaudhri et al. |
| 2015/0081325 A1 | 3/2015 | Pletcher et al. |
| 2015/0339446 A1 | 11/2015 | Sperling et al. |
| 2016/0132645 A1 | 5/2016 | Charpentier et al. |
| 2016/0212147 A1 | 7/2016 | Palin et al. |
| 2016/0246946 A1 | 8/2016 | Haley |
| 2017/0161433 A1 | 6/2017 | Perretta |
| 2019/0333614 A1 | 10/2019 | Burger et al. |
| 2020/0176098 A1 | 6/2020 | Lucas et al. |

FOREIGN PATENT DOCUMENTS

| | | |
|---|---|---|
| CN | 106663145 A | 5/2017 |
| WO | 2019/067089 A | 4/2019 |

OTHER PUBLICATIONS

"Notification of the First Office Action," mailed Sep. 9, 2023 in Chinese Application No. 202080033559.8. 7 pages.

"International Search Report and Written Opinion," mailed Sep. 1, 2020 in in International Application No. PCT/US2020/035361. 12 pages.

"Notice of Allowance," mailed Jun. 10, 2022 in U.S. Appl. No. 16/888,556. 12 pages.

"Final Office Action," mailed Jun. 2, 2023 in U.S. Appl. No. 16/888,592. 16 pages.

"Non-Final Office Action," mailed Jun. 9, 2022 in U.S. Appl. No. 16/888,592. 14 pages.

"Notice of Allowance," mailed Dec. 12, 2022 in U.S. Appl. No. 17/883,916. 12 pages.

"Notice of Allowance," mailed Jun. 5, 2023 in U.S. Appl. No. 18/105,142. 12 pages.

"Final Office Action," mailed May 22, 2024, in U.S. Appl. No. 16/888,592. 22 pages.

* cited by examiner

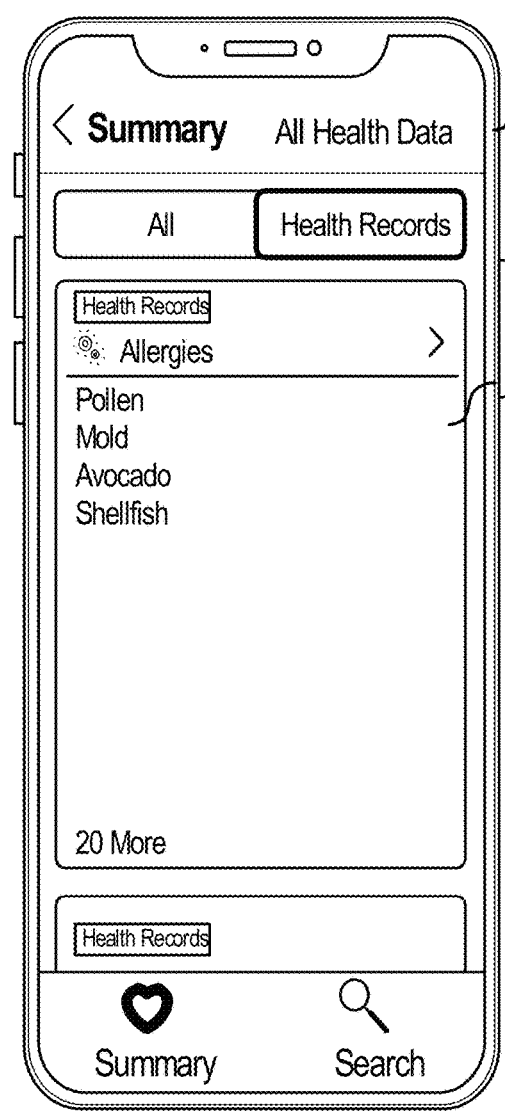
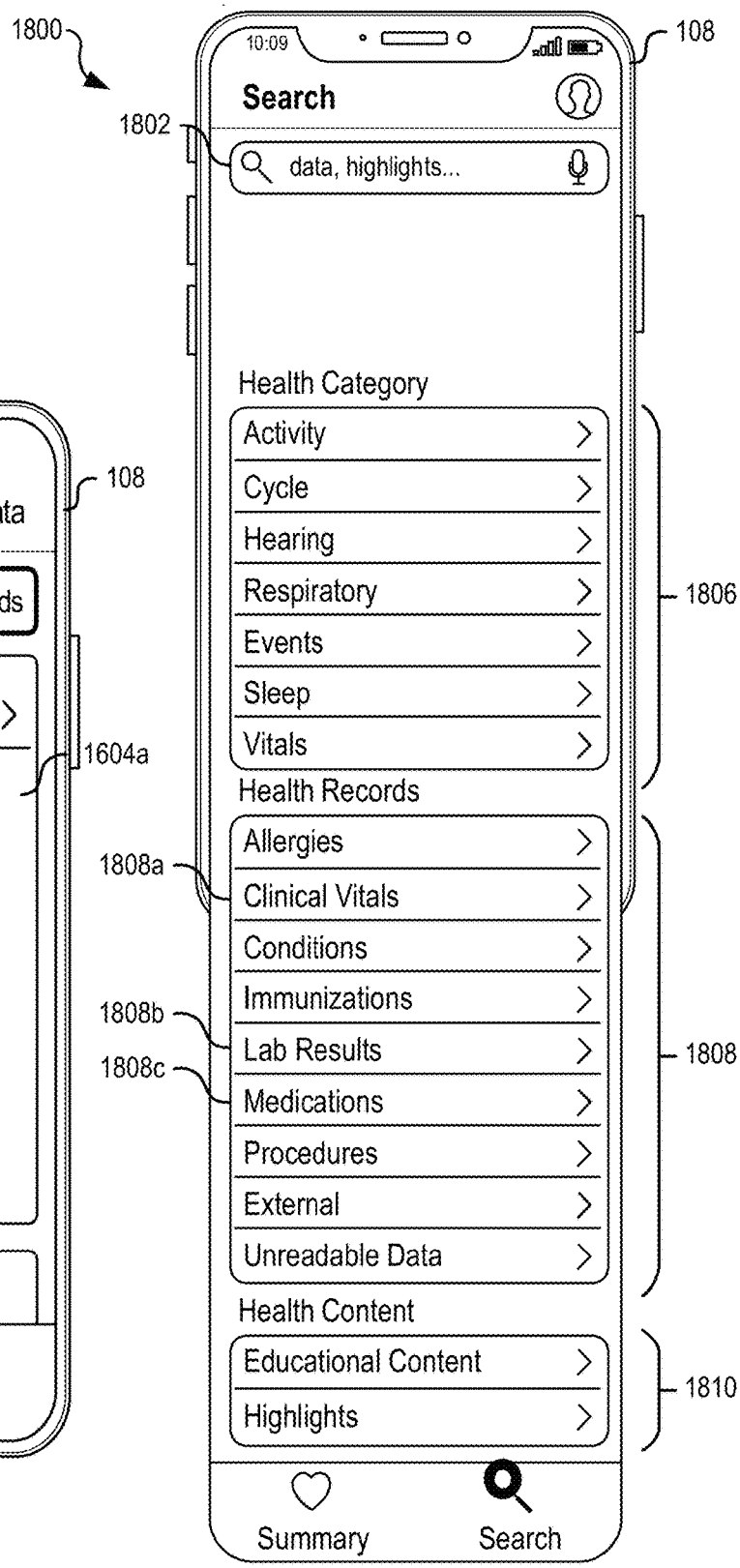
FIG. 17
FIG. 18

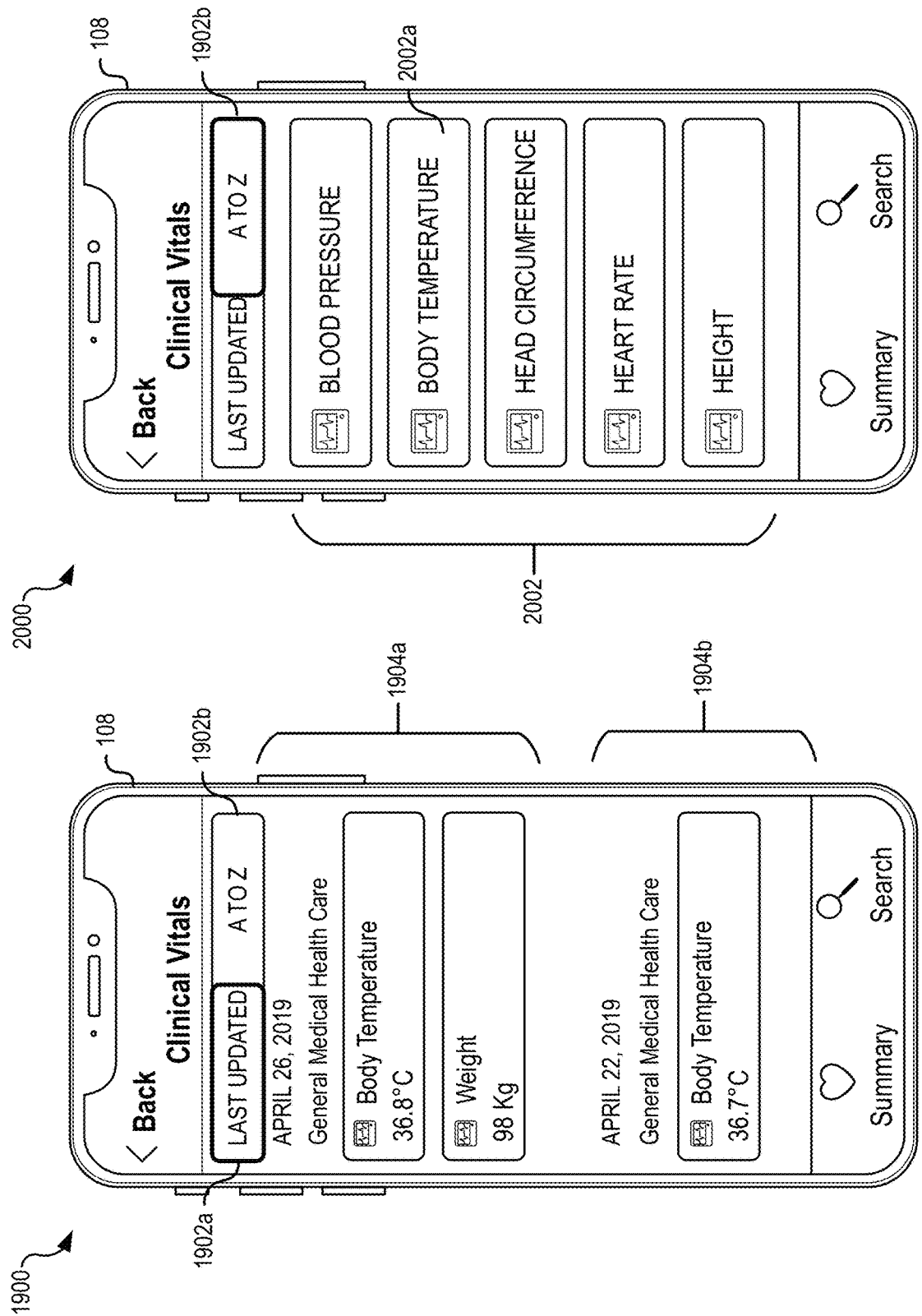

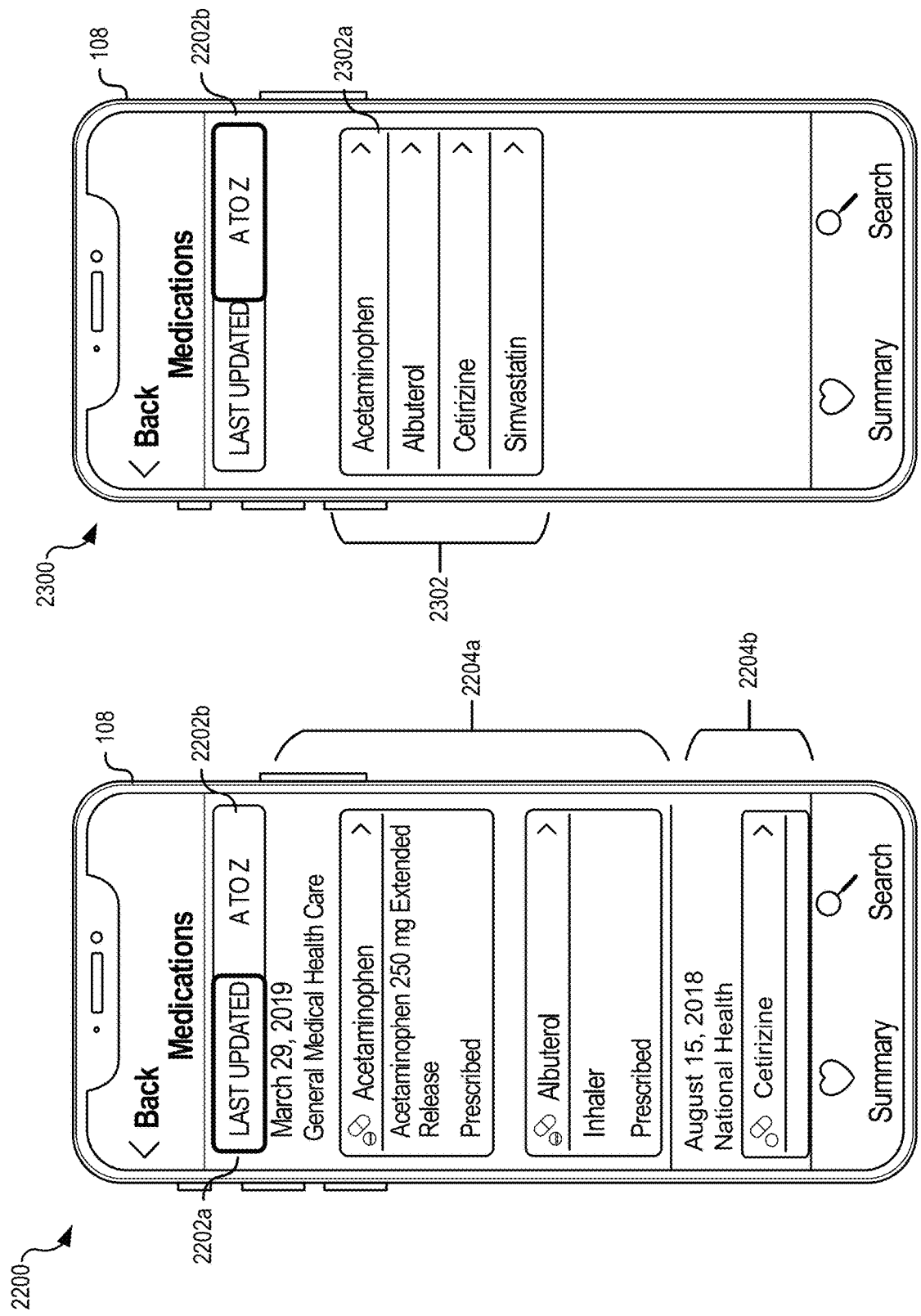

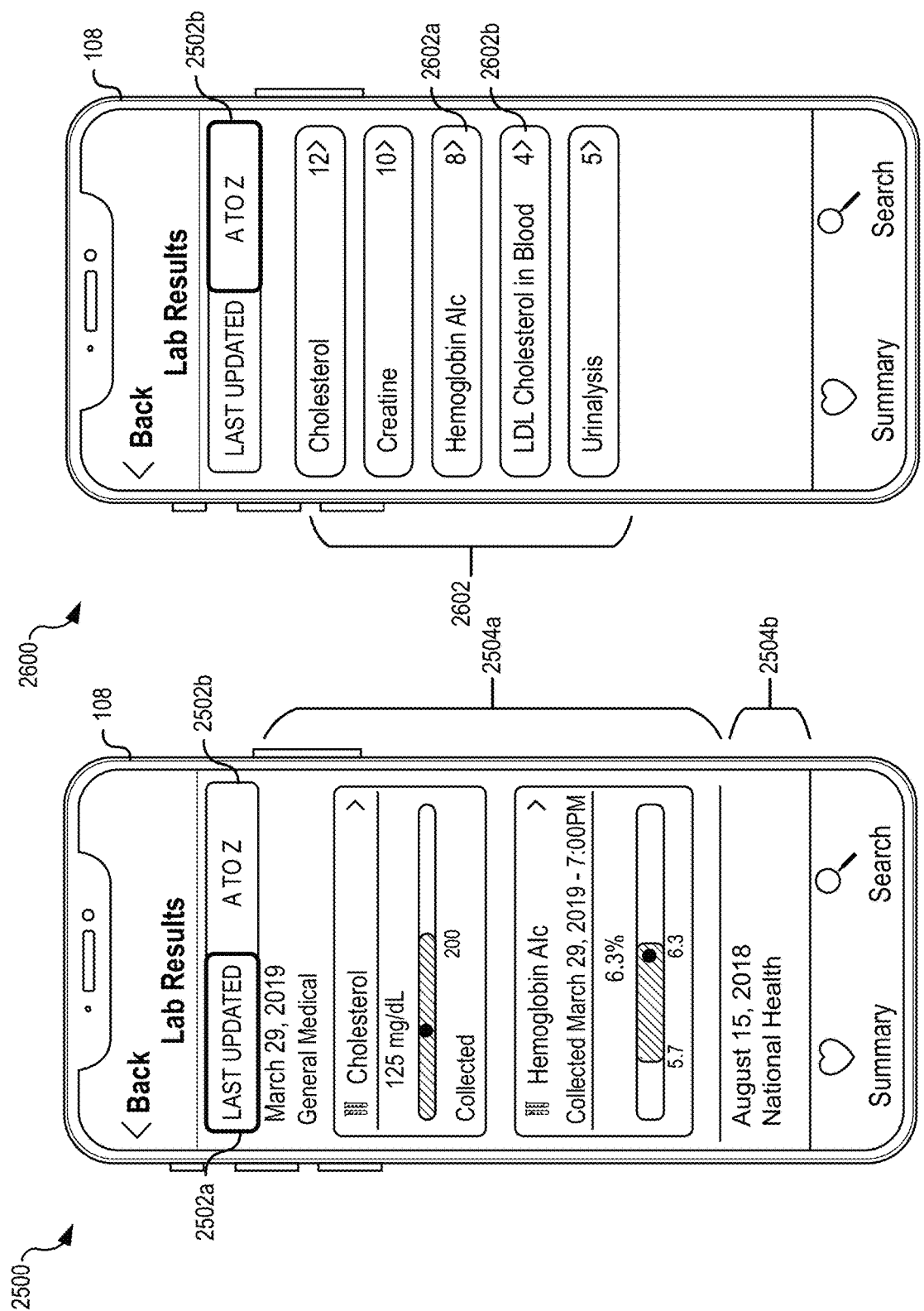

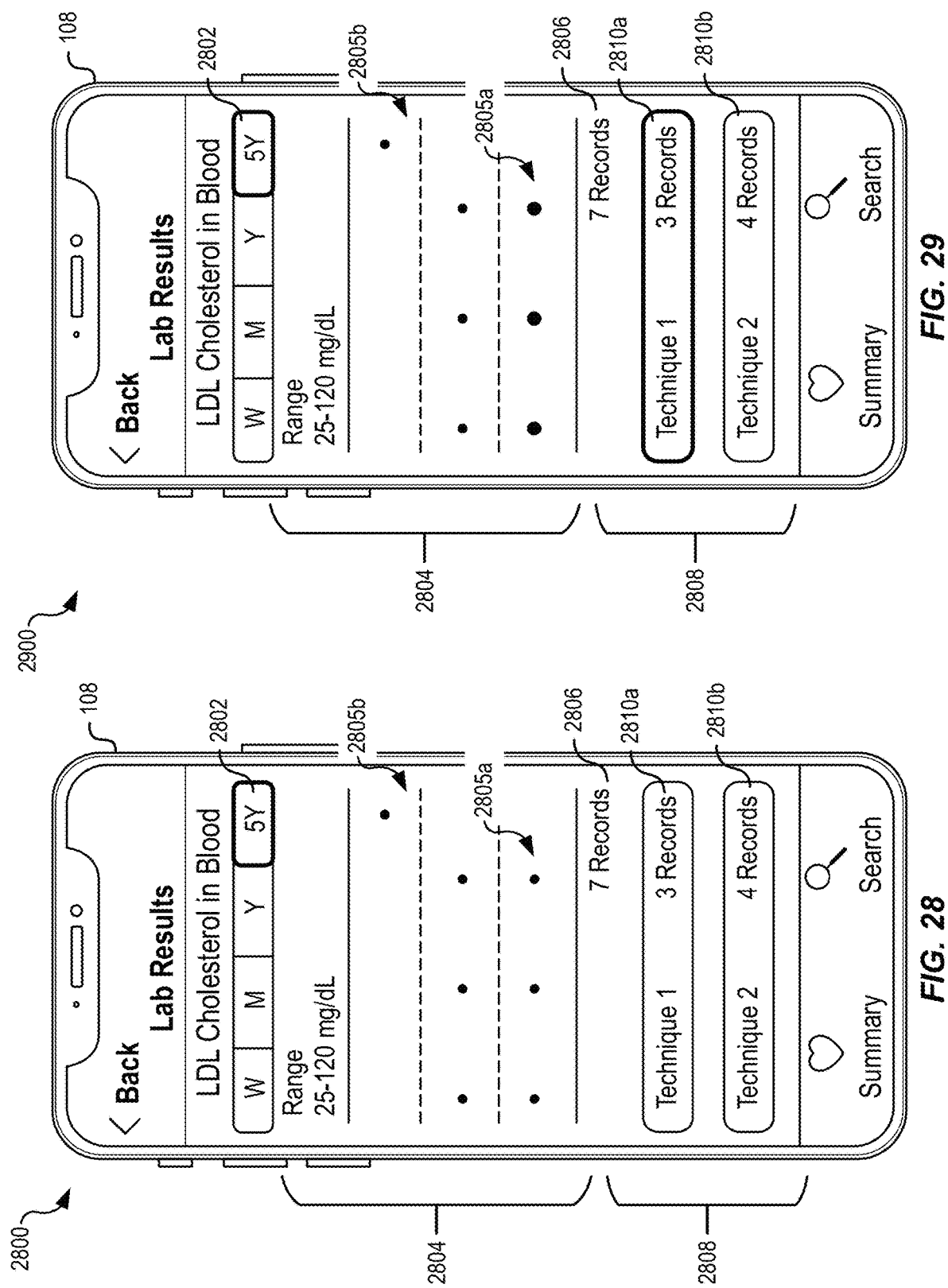

GENERATION OF CUSTOMIZED PERSONAL HEALTH ONTOLOGIES

CROSS-REFERENCES TO RELATED APPLICATIONS

This application is a continuation of U.S. patent application Ser. No. 18/105,142, filed Feb. 2, 2023, which is a continuation of U.S. patent application Ser. No. 17/883,916, filed Aug. 9, 2022 (now U.S. Pat. No. 11,636,931), which is a continuation of U.S. patent application Ser. No. 16/888,556, filed May 29, 2020 (now U.S. Pat. No. 11,475,984), which claims the benefit of U.S. Provisional Application No. 62/855,953, filed Jun. 1, 2019. These applications are incorporated by reference herein in their entirety.

BACKGROUND

Users typically visit more than one health institution (e.g., medical providers) to obtain medical treatment. For example, a user may periodically visit a neighborhood clinic for annual physical evaluations and for minor medical procedures. The neighborhood clinic may maintain an instance of the user's electronic health record (EHR) (e.g., a computer-stored and transferrable copy of a user's physical health record) using an EHR system, sometimes referred to as an electronic medical record (EMR) system. When the user visits the neighborhood clinic, a medical professional may update the electronic health record (e.g., record vital signs, identify prescriptions, order and record lab results, identify a diagnosis, etc.). However, other instances of the user's electronic health record may be maintained by other health institutions that are unaffiliated with the neighborhood clinic. These other health institutions may use different versions of the same EHR system or may even use completely different EHR systems (e.g., developed by different companies). Thus, instances of the user's electronic health record may be distributed among multiple health institutions. And, depending on which type and version of EHR systems used by the health institutions as well as provider preferences for recording health record data, health record data within each instance may be formatted, coded, and/or stored differently.

BRIEF SUMMARY

One general aspect includes a computer-implemented method, including accessing health concept information corresponding to a standard health coding ontology, the standard health coding ontology including a set of health codes. The computer-implemented method also includes accessing augmentation information from at least one augmentation source, the augmentation information corresponding to at least one health concept. The computer-implemented method also includes generating, using one or more transformer engines and based at least in part on the augmentation information, associations between health codes of the set of health codes and portions of the augmentation information. The computer-implemented method also includes generating a curated health ontology based at least in part on the associations, the curated health ontology including a plurality of concept nodes. The computer-implemented method also includes transmitting at least a portion of the curated health ontology to a requesting system for presentation or storage of health record data. Other examples of this aspect include corresponding computer systems, apparatus, and computer programs recorded on one or more computer storage devices, each configured to perform the actions of the methods.

One general aspect includes a computer-implemented method, including: receiving a set of selection criteria corresponding to a curated health ontology, the curated health ontology including a plurality of concept nodes each representing a health concept. The computer-implemented method also includes determining a subset of the plurality of concept nodes based at least in part on the set of selection criteria; generating a curated health sub-ontology that includes the subset of concept nodes by at least: identifying the subset of concept nodes from the curated health ontology, and combining the subset of concept nodes to define the curated health sub-ontology. The computer-implemented method also includes transmitting the curated health sub-ontology to a consuming system. Other examples of this aspect include corresponding computer systems, apparatus, and computer programs recorded on one or more computer storage devices, each configured to perform the actions of the methods.

One general aspect includes a computer-implemented method, including: accessing health record data stored on a user device and associated with a user profile corresponding to the user device, the health record data including a plurality of health record codes corresponding to at least one of a standard health coding ontology or a standard health coding terminology. The computer-implemented method also includes accessing a curated health sub-ontology stored on the user device, the curated health sub-ontology including a plurality of concept nodes. The computer-implemented method also includes generating an entry in a personal health ontology that at least associates a health record code of the plurality of health record codes with a concept node of the plurality of concept nodes. The computer-implemented method also includes storing the entry in the personal health ontology on the user device. Other examples of this aspect include corresponding computer systems, apparatus, and computer programs recorded on one or more computer storage devices, each configured to perform the actions of the methods.

One general aspect includes a computer-implemented method, including: receiving, at a user device, a request to view a user interface configured to present health record data stored on the user device and associated with a user profile corresponding to the user device. The computer-implemented method also includes accessing a personal health ontology stored on the user device that represents associations between health record codes of the health record data and concept nodes of a curated health sub-ontology stored on the user device, the personal health ontology specific to the user profile. The computer-implemented method also includes causing presentation of the user interface at the user device based at least in part on information from the personal health ontology. Other examples of this aspect include corresponding computer systems, apparatus, and computer programs recorded on one or more computer storage devices, each configured to perform the actions of the methods.

One general aspect includes a computer-implemented method, including: receiving, at a user device, a request to view a user interface including a graph that represents observable values from health record data stored on the user device, the health record data associated with a user profile corresponding to the user device. The computer-implemented method also includes accessing a personal health ontology stored on the user device, the personal health ontology representing associations between the observable values and one or more concept nodes of a curated health sub-ontology stored on the user device. The computer-implemented method also includes determining that at least one observable value of the observable values is of a type of data for which a filter exists by at least accessing the personal health ontology. The computer-implemented method also includes adding a filter to the at least one observable value. The computer-implemented method also includes causing presentation, at the user device, of the user interface including the graph with the filter applied to the at least one observable value. Other examples of this aspect include corresponding computer systems, apparatus, and computer programs recorded on one or more computer storage devices, each configured to perform the actions of the methods.

BRIEF DESCRIPTION OF THE DRAWINGS

FIG. 17 illustrates a user interface for presenting selected health record data on a user device using a personal health ontology, according to at least one example.

FIG. 18 illustrates a user interface for presenting selected health record data on a user device using a personal health ontology, according to at least one example.

FIG. 19 illustrates a user interface for presenting selected health record data on a user device using a personal health ontology, according to at least one example.

FIG. 20 illustrates a user interface for presenting selected health record data on a user device using a personal health ontology, according to at least one example.

FIG. 22 illustrates a user interface for presenting selected health record data on a user device using a personal health ontology, according to at least one example.

FIG. 23 illustrates a user interface for presenting selected health record data on a user device using a personal health ontology, according to at least one example.

FIG. 25 illustrates a user interface for presenting selected health record data on a user device using a personal health ontology, according to at least one example.

FIG. 26 illustrates a user interface for presenting selected health record data on a user device using a personal health ontology, according to at least one example.

FIG. 28 illustrates a user interface for presenting selected health record data on a user device using a personal health ontology, according to at least one example.

FIG. 29 illustrates a user interface for presenting selected health record data on a user device using a personal health ontology, according to at least one example.

DETAILED DESCRIPTION

Figure 1:
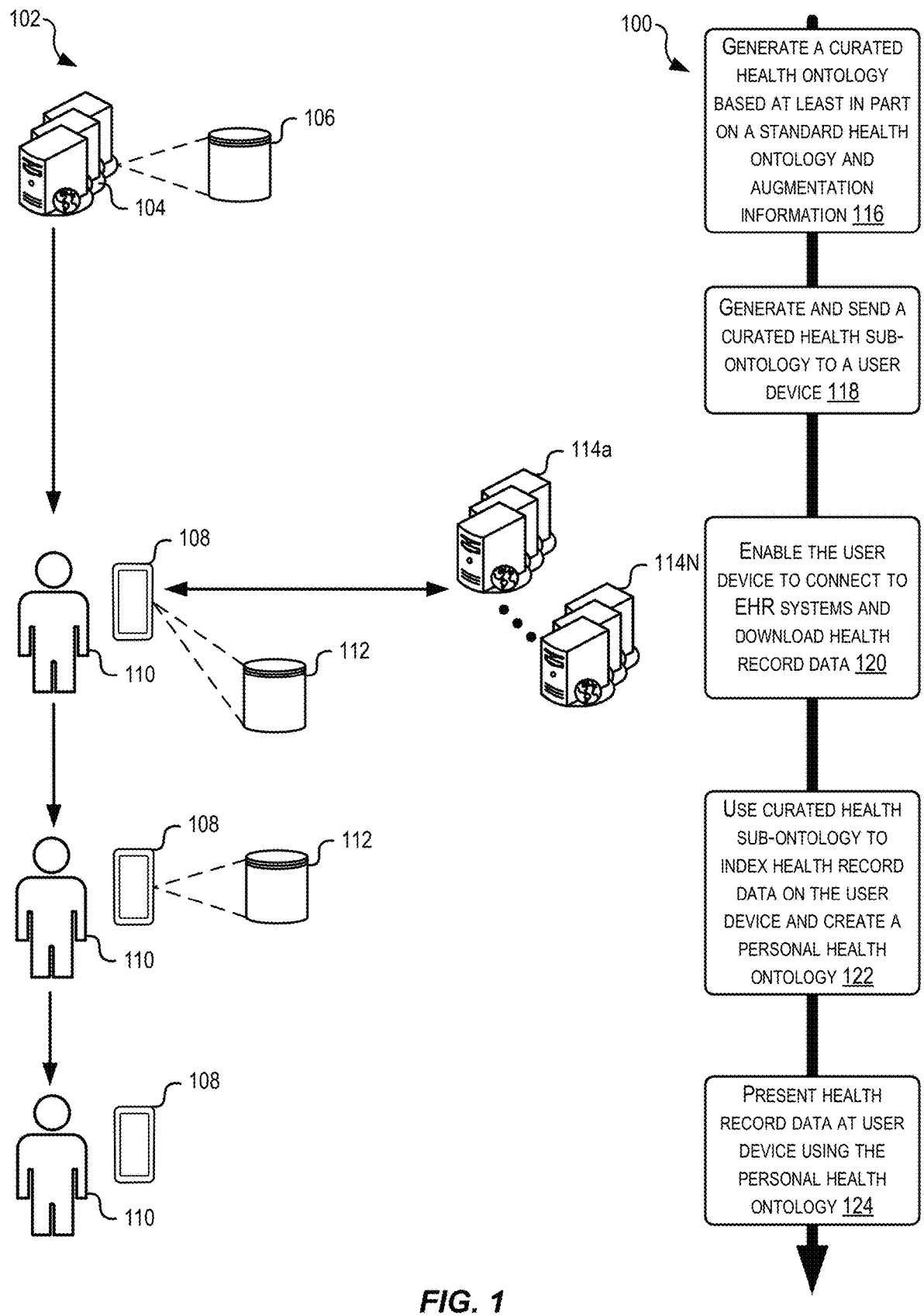
FIG. 1 illustrates a block diagram and a flowchart showing an example process for generating a curated health ontology and using portions of the curated health ontology to organize, store, and present health record data on user devices, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, devices, and computer-readable media for generating curated health ontologies, outputting sub-ontologies based on the ontologies, processing electronic health record data from disparate instances of a health record to enable efficient storage and retrieval thereof on user devices, and presenting health record data from the instances of the electronic health record in a uniform manner using a health application of a user device. Users to whom the electronic health records belong typically visit different health institutions as part of obtaining medical treatment. These health institutions may be part of the same provider organization (e.g., a clinic and a hospital owned by the same entity) or may be part of different organizations (e.g., a dialysis clinic owned by a first entity and an imaging center owned by a second entity). Each of these health institutions may maintain an instance of a particular user's electronic health record using an EHR system.

Some health institutions may provide web portals (e.g., patient portals) that allow users to view and/or otherwise interact with their respective electronic health records. However, because the medical industry is made up of many different organizations and because users tend to obtain care from different organizations, it is very unlikely that a single web portal will have a complete electronic health record for every user. Instead, users will likely have to access multiple web portals to get a complete view of their health record. Even if the user is able to access multiple web portals to view their health record, because of the idiosyncrasies of the health institutions relating to coding, indexing, and otherwise storing the health records, comparing the data from one portal to another may prove challenging, even when the records may represent similar facts.

The EHR systems that host the web portals may be configured differently from one another. For example, data storage formats, user and administrator functionality, and coding schemas may be unique to each. The techniques described herein enables individual, ongoing data pipelines to be established with each of these disparate sources. Once a pipeline is connected, the techniques described provides a platform for normalizing the data storage formats, user and administrator functionality, and coding schemas from these disparate sources. Thus, once each pipeline has been connected, the data may be stored on a user device in a uniform format, with a predefined set of user functionality, and according to a single coding schema. Doing so results in not only a technical improvement to a computing device, but does so in a way that stores data from the disparate sources in an optimized manner. The data is optimized as to storage capacity and storage access. Because of this, the computing device operates more efficiently than other devices that access electronic health records. This effectively frees up other computing resources for performing other processes.

Turning now to a particular example, to enable consistent organization and presentation of health record data from disparate sources, techniques are described for generating a curated health ontology. The curated health ontology is a concept-based ontology that is organized by nodes representing health concepts (e.g., concept nodes). The curated health ontology is generated by an ontology management system. The ontology management system begins to generate the curated health ontology by leveraging concept definitions from a robust standard health coding ontology such as the SNOMED® Clinical Terms (CT) standard or other similar health coding ontology. The ontology management system also accesses augmentation information from various additional sources (e.g., augmentation sources) to augment the data originally sourced from the standard health coding ontology. For example, information about standard health coding terminologies, input from subject matter experts, information from third-party data sources, and other information can be leveraged to add nodes beyond those provided by the standard health coding ontology, augment relationships between nodes, add attributes to nodes, and add new concept nodes. As part of adding the augmentation information to the curated health ontology, the augmentation information is passed through transformers specific to the augmentation source. The transformers extract, transform, and load the information.

Because the curated health ontology is generated using existing standards and augmented in a customized way, the curated health ontology may be a comprehensive and exhaustive representation of many, if not all, health concepts and their corresponding relationships. However, depending on how the curated health ontology is intended to be used, only a portion of the curated health ontology may be relevant. For example, it may be determined which portions of the ontology would be needed by a consuming system given some set of selection criteria. The ontology management system described herein provides a mechanism for consuming systems (e.g., any suitable device, system, interface, application, etc.) to request a sub-ontology based on the curated health ontology (e.g., a curated health sub-ontology), and to do so in a privacy protecting manner. A user device or other system associated with the consuming system may input a set of selection criteria. The ontology management system uses the set of selection criteria to traverse the curated health ontology and identify which concept nodes and associated relationships should be included in the curated health sub-ontology. As this information is identified, the curated health sub-ontology is built by the ontology management system.

The curated health sub-ontology may be shared with the user device or other system associated with the consuming system in any suitable manner. For example, if the consuming system is a user device, the curated health sub-ontology may be transmitted to the user device along with an operating system update or may be transmitted to the user device over the air outside of a typical update cycle (e.g., when the user device is plugged into a charger and connected to a WiFi network).

In some examples, the curated health ontology, which may be a graph database, may be selectively downloaded using a set of curated anonymizing hash operations. Use of the curated anonymized hash operations may contribute to protecting the privacy of the user of the user device with respect to the ontology management system. Each anonymizing hash operation may be curated and/or otherwise tailored to a particular health coding ontology used to originally encode health record data (e.g., by the system that created the data), which is now stored on the user device. When the user device gets new health record data, the user device may identify the relevant health coding ontology and, from the relevant ontology, identify which codes are used to identify the new health record data. Once this information has been identified, the user device may then select and use the respective curated anonymizing hash operation to request information for the identified codes from the ontology management system. In some examples, the user device requests the information by asking the ontology management system for the particular page identifiers associated with the identified codes. For example, the hash operation may enable the user device to determine the page identifiers based on the particular codes associated with the health record data. Unlike conventional database sharding approaches, the anonymizing hash operation may enable the user device to obtain overlapping portions of the health ontology, and the user device may be configured to resolve the overlaps.

The user device may use an application such as a computer application configured to manage health record data, including downloading and storing the curated health sub-ontology, on the user device. The user device can be used to access a provider Web system that maintains a database of health institutions that participate in health record sharing. Once a health institution has been identified by searching in the database, the user device obtains information from the provider Web system that enables the user device to establish a unique connection with a gateway associated with the identified health institution. The gateway is an endpoint of the EHR system associated with the health institution. The gateway is used to share health record data with the user device using an industry standard format such as Fast Healthcare Interoperability Resources (FHIR®) created by the Health Level Seven (HL7®) International standards organization. This same process can be repeated to download health record data from different EHR systems of different health institutions. The techniques described herein use the curated health sub-ontology to process health record data from different health institutions to create a personal health ontology that is specific to the user. The personal health ontology may represent an index that maps items from the user's health record to concept nodes in the curated health sub-ontology. The personal health ontology can be queried (e.g., by the user device or some other system) to obtain information about specific aspects of the user's health record. For example, the personal health ontology can be queried by a third-party application to determine whether any active medications represented in the health record are within a drug interaction categories (e.g., contraindicated, serious, significant, or minor).

In some examples, new nodes and/or node annotations may be added to the personal health ontology in real-time, which may be responsive to queries or requests, using a set of heuristics, and/or in a probabilistic manner. An example probabilistic annotation may include a probability that the user has a certain condition given other information present in the ontology. Suggestions and/or recommendations may be presented at a user interface based on the annotations and/or new nodes. For example, if the condition is a heart-related condition, the recommendation may include adjustments to diet or increasing activity levels, both of which may be tracked by the user device 108 and used to update the respective nodes.

As an additional example, if the health record information identifies a lab result, and the user has a predefined condition as reflected by the ontology, the user device may determine that the user is at risk of something else (e.g., a different condition, a complication, etc.). These other risks may be presented to the user at the user interface. Such recommendations may rely primarily upon heuristics to ensure that any recommendations are repeatable and the data used to make the recommendation can be identified, as compared to a probabilistic approach prepared using predictive modeling.

The user device also uses the personal health ontology for presenting the health record data on the user device. This can include presenting the data according to a categorization based on a set of predefined categories (e.g., allergies, vitals, conditions, immunizations, lab results, medications, and procedures). Within each category, the personal health ontology may be used to provide additional organizational benefits. In a medication category, for example, an "A to Z" list of medications may be created, which represents all medications found in the health record data organized under a single medication heading. The single medication heading (e.g., acetaminophen) may represent items from different instances of the health record including health record data that was originally coded using different standards, included different display strings, identified a generic or a name brand drug, included different dosage instructions, etc. The presentation of the different items may be normalized using the personal health ontology. For example, items representing prescription "Tylenol 500 mg daily oral" and "500 MG acetaminophen oral taken daily," which are medically identical, may be represented in a uniform way (e.g., "Tylenol 500 MG oral daily"). In this manner, similar items in the instances of the electronic health record can be grouped together, identified during a search, and otherwise used for comparison.

The personal health ontology may also be used to graph or otherwise compare certain types of health record data (e.g., vitals, labs, or other such observable values) in a way that captures nuances in how the observable values were obtained. This includes representing things such as the type of test used and the conditions under which the test was administered. The test results depend on this information. For example, two tests for cholesterol may each produce a different observed value, which according to their respective scales, may be normal. However, if the results from the two tests were presented according to the same scale (e.g., the first scale), the results from the second test may appear abnormal. The benefits of showing multiple tests results over some period of time, however, may outweigh the small potential for confusion. To reduce this potential, the personal health ontology is leveraged to create graphical filters to automatically highlight certain differences in test result data (e.g., a type of test used to obtain the data). A user can toggle between different filters to highlight which data points were obtained using which test type.

The systems, devices, and techniques described herein provide several technical advantages that improve the functioning of server computers that generate curated health ontologies and user devices that index, organize, and present health record data. For example, using curated health sub-ontologies on the user devices instead of downloading complete curated health ontologies to the user device results in processing savings and storage savings on the user devices.

Because a curated health sub-ontology is optimized for a user device (e.g., optimized for the type of consuming system based on a set of selection criteria), both in terms of content and overall size, fewer processing resources are required for traversing the curated health sub-ontology during indexing and/or during content presentation. This effectively frees up processing resources for other applications and/or other processes running on the user device. Additionally, because the user device uses a personal health ontology that is customized to the health record data on the user device (e.g., created from the curated health sub-ontology based specifically on the health record data downloaded to the user device), the presentation of the health record data is more efficient as compared to conventional approaches. This is especially true because the personal health ontology can include entries corresponding to "pre-walks" of the curated health sub-ontology (e.g., preprocessed traversals through the curated health sub-ontology associated with one or more health concepts). These "pre-walks," which can be performed as background processes, effectively configure the personal health ontology for even more efficient presentation of the health record data because the user device is not required to traverse the path when the concept data associated with the path is requested for presentation. Additionally, because the user device downloads the sub-ontology from the server computers, the user device does not need to constantly query the server computers for information from the curated health ontology. This results in the technical advantage of bandwidth savings realized at the server computers and at the user device.

Turning now to the figures, FIG. 1 illustrates a block diagram 102 and a flowchart showing a process 100 for generating a curated health ontology and using portions of the curated health ontology to organize, store, and present health record data on user devices, according to at least one example. The diagram 102 includes an ontology management system 104. The ontology management system 104 is any suitable combination of computing devices such as one or more server computers, which may include virtual resources, capable of performing the functions described with respect to the ontology management system 104. Generally, the ontology management system 104 is configured to manage aspects of generating curated health ontologies and sharing portions of these ontologies. The ontology management system 104 may be associated with a health ontology storage 106. The health ontology storage 106 is configured to store the curated health ontologies and associated information relating to generating the curated health ontologies and sharing portions thereof.

The diagram 102 also includes a user device 108, which is any suitable electronic user device capable of communicating with other electronic devices over a network such as the Internet, a cellular network, or any other suitable network. In some examples, the user device 108 may be a smartphone or other user device on which specialized applications can operate. The user device 108 is associated with or otherwise operated by a user 110. The user 110 is an example of a patient whose electronic health records are the subject of this specification. The user device 108 includes health record storage 112 configured to store health record data, portions of curated health ontologies, a personal health ontology, and any other suitable information.

The diagram 102 also includes one or more electronic health record (EHR) systems 114. Each EHR system 114 is associated with at least one health institution and used to manage electronic health record data from the institution. In some examples, a single EHR system 114 is associated with multiple health institutions and used to manage electronic health record data from the multiple institutions. In particular, the EHR system 114 may store, organize, and/or otherwise manage health record data generated by medical professionals of the health institutions. The EHR system 114 may include one or more gateways, each including one or more endpoints to enable multiple connections between the EHR system 114 and other electronic devices. In some examples, user devices such as the user device 108 may interact with the EHR system 114 using any suitable interfaces such as gateway application programming interfaces (API) or via patient portals including graphical user interfaces. The gateway APIs may define a set of function calls for communications between the EHR system 114 and the user device 108.

FIGS. 1, 5, 6, 7, 8, 9, 12, 13, 14, 30, and 31 illustrate example flow diagrams showing processes 100, 500, 600, 700, 800, 900, 1200, 1300, 1400, 3000, and 3100, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

Figure 4:
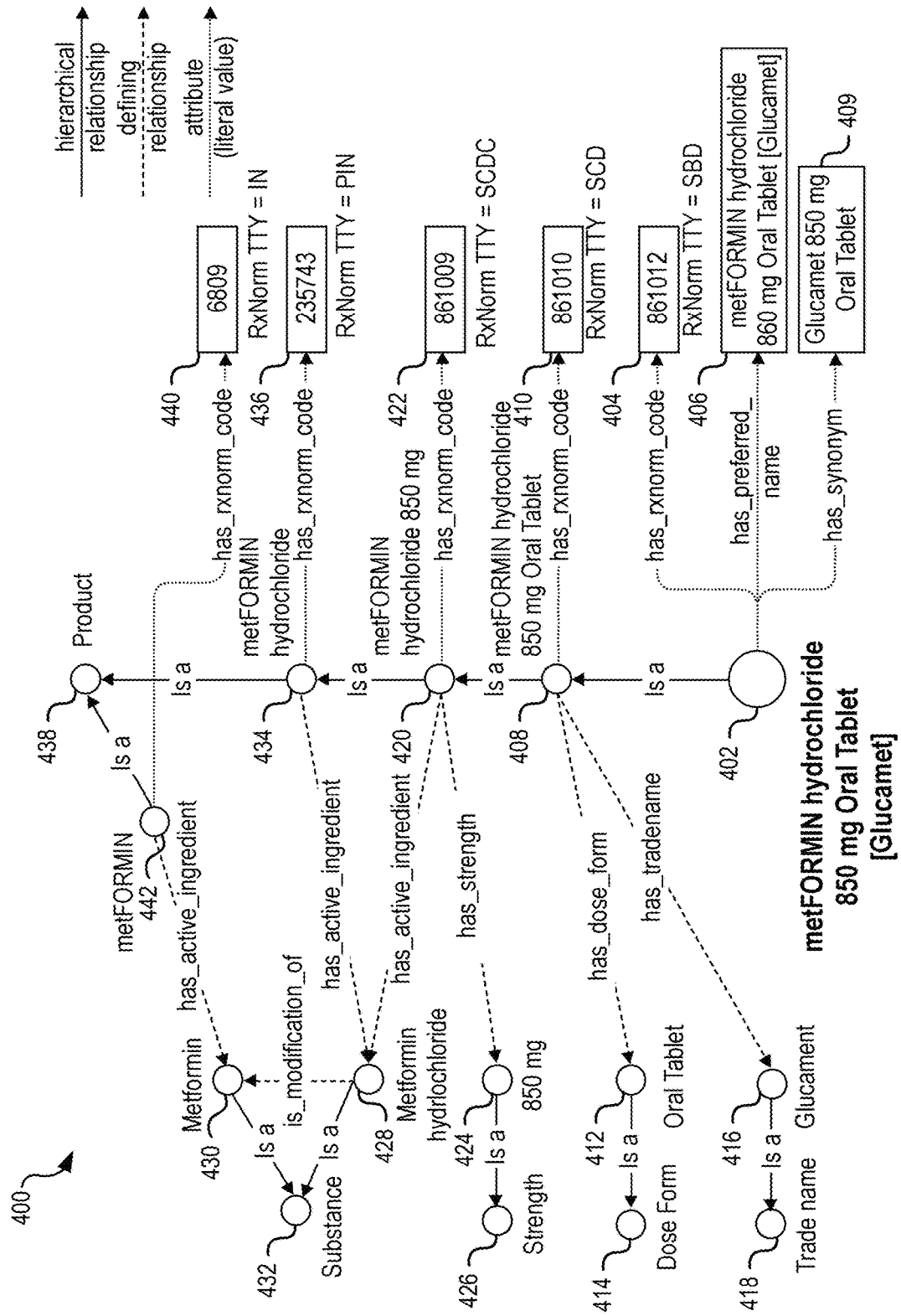
FIG. 4 illustrates a diagram showing an example curated health ontology for storing relationships and attributes of a health concept, according to at least one example.

The process 100 begins at 116 by the ontology management system 104 generating a curated health ontology based at least in part on a standard health ontology and augmentation information. As described herein, the ontology management system 104 obtains information about the standard health ontology and the augmentation information from one or more external sources and uses the information to generate the curated health ontology. The ontology management system 104 stores the curated health ontology in the health ontology storage 106. FIG. 4 illustrates an example of a curated health ontology.

At 118, the process 100 includes the ontology management system 104 generating and sending a curated health sub-ontology to a user device. In some examples, the curated health sub-ontology is generated based on a set of selection criteria received from the user device. The curated health sub-ontology includes a subset of the concept nodes of the curated health ontology. The curated health sub-ontology can be tailored to the user device or other consuming system.

The user device referenced in block 118 may be the user device 108. As described herein, the ontology management system 104 is configured to send the curated health sub-ontology to the user device 108 in any suitable manner.

At 120, the process 100 includes enabling the user device 108 to connect to the EHR systems 114 to download health record data. The user device 108 stores the health record data in the health record storage 112. In some examples, connecting to the EHR system 114 may include enabling the user device 108 to access a server system discussed in FIG. 2 to search a database of health institutions. The user device 108 may submit queries to the system to identify health institutions associated with the user 110. These queries may be transmitted to the server system. The user device 108 may connect to the EHR system 114 using the information about the EHR system 114 received from the server system. Downloading health record data may include downloading electronic health records using the FHIR standard or any other suitable standard for transporting health records. In some examples, the user device 108 may connect to and download electronic health record data from more than one EHR system 114. Patient privacy is maintained because the server system does not store any health record data. Instead, the server system simply "connects" the EHR system 114 and the user device 108, and the user device 108 securely downloads the health record data and stores it securely on the user device 108.

At 122, the process 100 includes the user device 108 using the curated health sub-ontology to index health record data on the user device 108 and to create a personal health ontology. In some examples, this may include the user device 108 determining associations between nodes of the sub-ontology and codes referenced in the electronic health record data. These associations, sometimes referred to as mappings, are used to form the personal health ontology, which may also be stored in the health record storage 112.

The personal health ontology may also include mappings and/or dedicated nodes based on sensor data and/or demographic data obtained from a profile of the user 110. For example, the user device 108 and/or an accessory user device (e.g., a watch or other wearable sensor device that shares its data with the user device 108) may include sensors such as a motion sensor/accelerometer, ambient light sensors, gyroscopes, location sensor/GPS, facial recognition sensor(s), heart rate sensors (e.g., optical and/or electrical), barometric altimeter, compass, and any other suitable sensor. Data from these sensors, which may be managed by an application on the user device 108, may be used to add nodes to the personal health ontology, augment relationships between nodes, and/or annotate nodes with additional information. All of this information may be surfaced at the user device 108 in the manner described herein.

At 124, the process 100 includes the user device 108 presenting health record data at the user device 108 using the personal health ontology. In some examples, a health user interface is used to present the health record data. The personal health ontology is referenced and, in some examples, the curated health sub-ontology is referenced as part of presenting the health record data. Presenting the health record data may include categorizing the data, applying filters to the data, normalizing portions of the data, and/or performing any other suitable operation on the data to provide for consistent display and organization.

Figure 2:
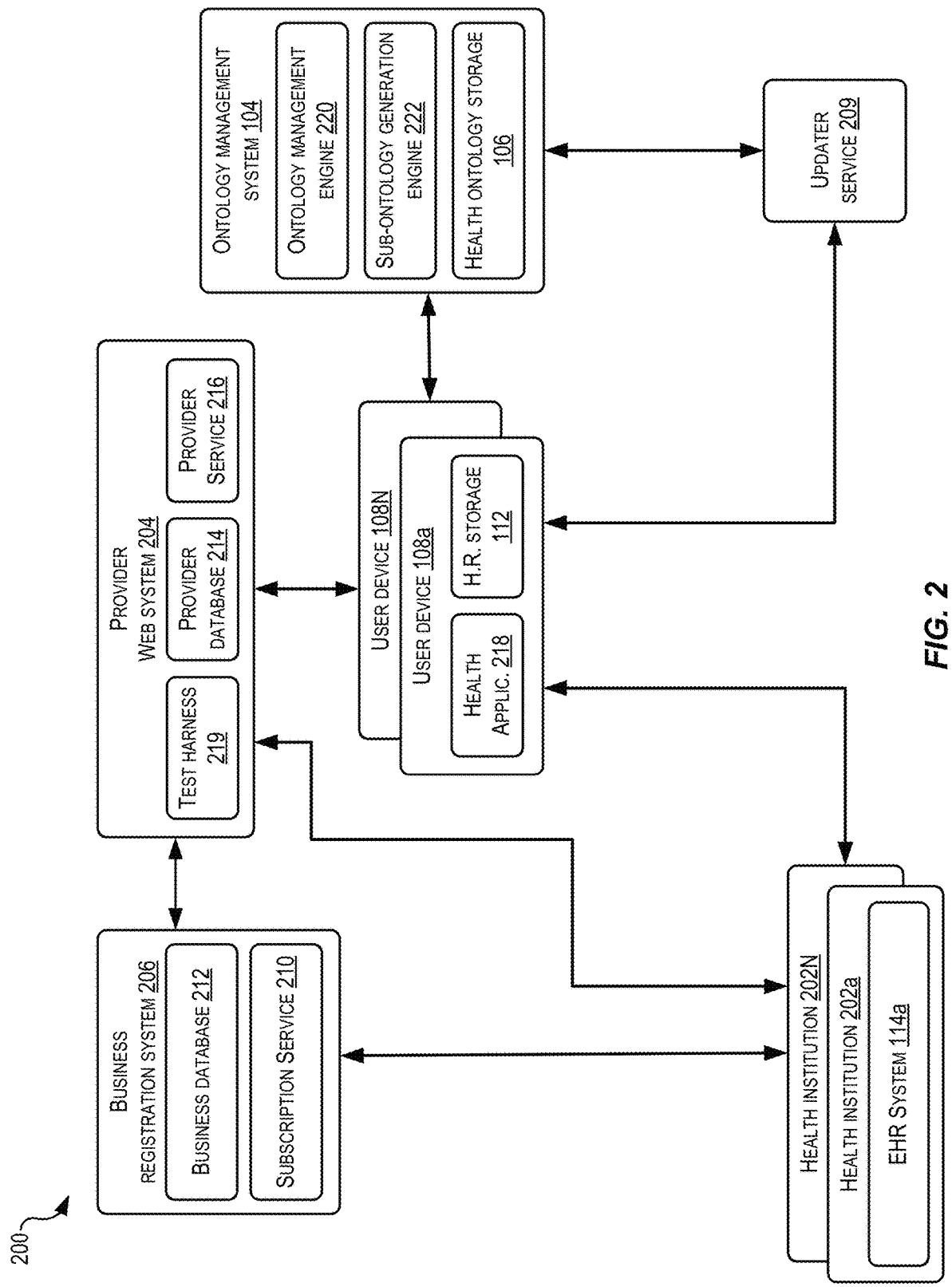
FIG. 2 illustrates a block diagram showing an example architecture or system for enabling storage and retrieval of electronic health records on user devices, according to at least one example.

FIG. 2 illustrates a block diagram showing an example architecture or system 200 for enabling storage and retrieval of electronic health records on user devices, according to at least one example. The system 200 includes a few elements introduced in FIG. 1. In particular, the system 200 includes the ontology management system 104, one or more user devices 108*a*-108N (e.g., any suitable number of user devices), one or more EHR systems 114*a*-114N (e.g., any suitable number of EHR systems) associated with one or more health institutions 202*a*-202N, a provider Web system 204, a business subscription system 206, and an updater service 209. As appropriate and as illustrated by the arrows, the elements of the system 200 may be communicatively coupled via one or more suitable communication networks.

Beginning with the business subscription system 206, the business subscription system 206 may be any suitable collection of hardware and software components configured to collect, store, update, and otherwise manage business locations including those of the health institutions 202. For example, the business subscription system 206 may include a business database 212 and a subscription service 210 to enable subscription of the EHR systems 114 of the health institutions 202. When a health institution 202 is subscribed and active, the user devices 108 may be allowed to connect to and download health record data from the associated EHR system 114 (e.g., a gateway of the EHR system 114).

As part of subscribing and managing subscriptions, the subscription service 210 may include functionality to collect, store, update, and otherwise manage business locations. In some examples, the subscription service 210 provides one or more user interfaces by which authorized users of the health institution 202 may input information about their location. This information may include geographic information (e.g., a physical address and pin on a map), image information (e.g., logos), contact information (e.g., business, legal, technical, etc.), and any other information relating to a business. The subscription service 210 may also be configured to create and/or update record entries in the business database 212 based on information received. For example, an authorized user associated with the health institution 202 may share business information with the business subscription system 206. Once this information has been shared and validated, the business information may published for public consumption (e.g., indexed for searching, made available on a map platform, shared directly with users, etc.).

The business database 212 may maintain the collected business information and any relationships between entities represented by the business information. In some examples, because the business subscription system 206 may be used to register other business entities (not just health institutions 202), records for the health institutions 202 may be maintained in both the business database 212 and a provider database 214 maintained by the provider Web system 204. In some examples, the business subscription system 206 shares business information with the provider Web system 204 in any suitable manner.

Turning now to the provider Web system 204, the provider Web system 204 may include the provider database 214 introduced herein, a provider service 216, and a test harness 219. Generally, the provider Web system 204 may validate the EHR systems 114, maintain information about the health institutions 202 and associated EHR systems 114, enable searching of the health institutions 202 associated with the EHR systems 114, and manage access of the user devices 108 to the EHR systems 114. The provider Web system 204 may be implemented in the "cloud."

As part of subscribing a health institution 202, the test harness 219 of the provider Web system 204 may be used to test and/or otherwise validate that a test user using a test user device 108 can connect to and download data from the EHR system 114. In this manner, the test harness 219 may simulate actions that one of the user devices 108 may perform to connect to the EHR system 114. In some examples, the test harness 219 may test this connection when a health institution 202 is first subscribed and at other times after the initial subscription. For example, the connection may be tested periodically, when certain conditions are fulfilled, and under any other circumstance. If the test is positive, a status indicator(s) in the provider database 214 associated with the health institution 202, the EHR system 114, and/or a gateway associated with the EHR system 114 may be updated to reflect that the EHR system 114 or the gateway is/are active. If the test is negative, the status indicator(s) may be updated to reflect that the EHR system 114 is inactive. When active, the user devices 108 may be capable of connecting to the gateways of the EHR systems 114. When inactive, the user devices 108 may be unable to connect to the gateways of the EHR systems 114.

The provider service 216 may maintain information about the health institutions 202 and associated EHR systems 114 in the provider database 214, enable searching of the health institutions 202 associated with the EHR systems 114, and manage access of the user devices 108 to the EHR systems 114. In some examples, the user devices 108 send requests to search for the health institutions 202 to the provider service 216. The provider service 216 processes these requests and returns results. In some examples, as part of establishing a connection with one of the EHR systems 114, the user device 108 will check in with the provider service 216 to determine whether any configuration information associated with the EHR system 114 has changed. The configuration information, which may be stored in the provider database 214 may include API information, provider identifiers, status indicator information, and any other suitable information relating to the configuration of the EHR system 114 and/or other entities associated with the EHR system 114.

The user devices 108 may include a health application 218 and the health record storage 112. Generally, the user devices 108 may be associated with and operated by different users (e.g., patients of the health institutions 202). Functionally, the health application 218 may enable the user devices 108 to communicate with the provider Web system 204 (e.g., to search for the health institutions 202, obtain configuration information about the health institutions 202, and perform other techniques), communicate with the EHR systems 114 of the health institutions 202 (e.g., to download data packages including electronic health records and/or updates to electronic health records and to perform other such techniques), communicate with the ontology management system 104 (e.g., to download curated health sub-ontologies), communicate with the updater service 209 (e.g., to download curated health sub-ontologies and/or updates to the curated health sub-ontologies), and index and store downloaded health record data.

The ontology management system 104 may be configured to manage aspects of curating health record data for presentation at the user device 108 using the health application 218. To this end, the ontology management system 104 may include an ontology management engine 220, a sub-ontology generation engine 222, and the health ontology storage 106.

Generally, the ontology management engine 220 is configured to generate a curated health ontology as described herein. This may include accessing external (to the ontology management system 104) data sources to obtain data for use in generating the curated health ontology.

Generally, the sub-ontology generation engine 222 is configured to generate curated health sub-ontologies for consuming systems. Given storage and processing considerations, it may be impractical for the entire curated health ontology to be shared with consuming systems such as the user device 108. Thus, in some examples, the ontology management system 104, which may be Cloud-based system, may generate and share sub-ontologies. In some examples, the ontology management system 104 may host one or more APIs that can be used to access the ontology from the health ontology storage 106 to supplement the curated health sub-ontologies with additional information (e.g., concept nodes, attributes, metadata, etc.) from the health ontology storage 106. In this manner, the user device 108 can selectively download information from the health ontology storage 106 to the health record storage 112 in order to enhance the health record data already stored on the user device 108. This can be performed using the anonymized hash described herein.

The updater service 209 is configured to provide updates to the user devices 108. For example, the updater service 209 can include a mechanism for delivering updates to the user devices 108 as part of an operating system update, as part of an application update (e.g., an update to the health application 218), or in any other suitable manner (e.g., at a time when the user device 108 is connected to WiFi and plugged into a charger). In some examples, the updater service 209 may send portions of the ontology to the user device 108 as part of an update cycle.

Figure 3:
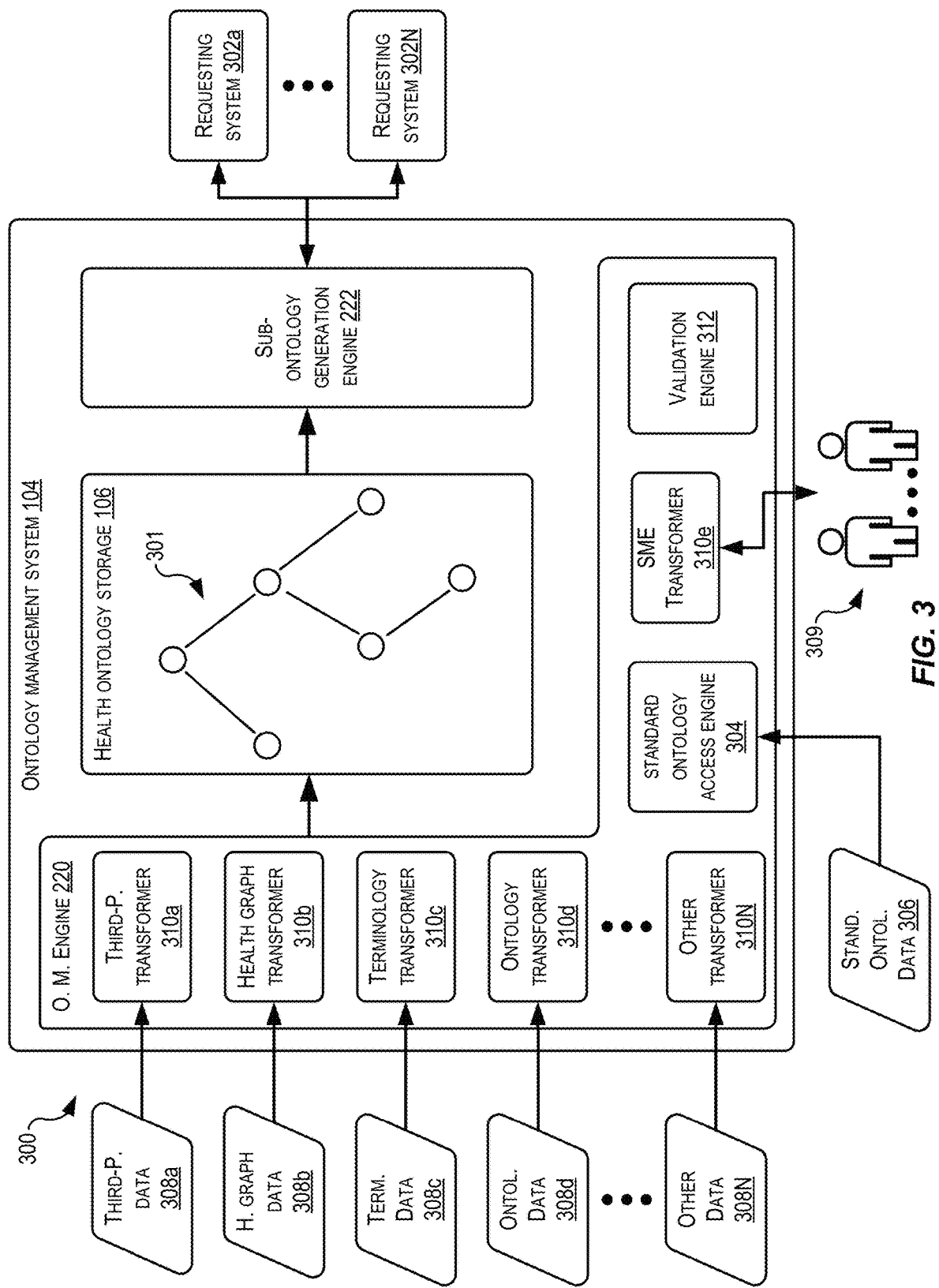
FIG. 3 illustrates a block diagram showing an example system for generating a curated health ontology, according to at least one example.

FIG. 3 illustrates a block diagram showing an example system 300 for generating a curated health ontology 301, according to at least one example. The system 300 includes the ontology management system 104, which includes the ontology management engine 220, the health ontology storage 106, and the sub-ontology generation engine 222.

Generally, the purpose of the ontology management system 104 is to generate the curated health ontology 301 and share portions of the ontology with one or more requesting systems 302a-302N. The ontology management engine 220 generates the curated health ontology 301 by using a standard ontology access engine 304 to access information from standard health coding ontology data 306. The standard health coding ontology data 306 may be hosted by a third-party server.

In some examples, the standard health coding ontology data 306 may include a set of health concepts organized ontologically such as the SNOMED® Clinical Terms (CT) standard ontology. Accessing the standard health coding ontology data 306 may include the ontology management system 104 connecting to an external data source that hosts the standard health coding ontology data 306 and downloading a file that includes the standard health coding ontology data 306. In some examples, a user device connects to the external data source, downloads the data 306, and uploads the data 306 to the ontology management system 104. In some examples, the standard health coding ontology data 306 is obtained using one or more API calls or via some other interface.

The standard ontology access engine 304, while illustrated as part of the ontology management engine 220, may, in some examples, be external to the ontology management engine 220. For example, standard ontology access engine 304 may be hosted by an ontology server associated with the data source of the standard health coding ontology data 306. In some examples, the data hosted on the ontology server may be accessible using one or more API calls or via some other interface.

The standard health coding ontology data 306 is used to seed the curated health ontology 301. For example, concept nodes, definitions, relationships, and the like from the standard health coding ontology data 306 may represent a baseline for the curated health ontology 301.

One or more external data sources 308 and subject matter experts 309 may be accessed by the ontology management engine 220 to augment and/or otherwise improve the curated health ontology 301. Such external sources may include third-party data 308a, health graph data 308b, terminology data 308c, ontology data 308d, and any other data 308N. The data sources 308 and the subject matter experts 309 are sometimes referred to as augmentation sources that provide augmentation information. The data sources 308b-308d are useable for accessing health coding standards.

Depending on the type of data represented by the external data sources 308, the ontology management engine 220 may include dedicated transformer engines 310 to transform the external data to data useable by the ontology management engine 220 to generate the curated health ontology 301. For example, the ontology management engine 220 may include a third-party data transformer 310a, a health graph transformer 310b, a terminology transformer 310c, an ontology transformer 310*d*, a subject matter expert (SME) transformer 310*e*, and an other transformer 310N. The transformer engines 310 may include Extract-Transform-Load (ETL) processes, which may be defined as at least three different classes, depending on the data source 308. For example, at least some transformers 310 may be configured to transform reference standards (e.g., the RxNorm® standard, Logical Observation Identifiers Names and Codes (LOINC) standard, vaccines administered data (CVX), etc.), others may be configured to transform ValueSets (e.g., FHIR ValueSets), and others may be configured to transform input from subject matter experts 308*e* (e.g., grouping health record items, charting health record data, and identifying suitable display strings for health record items).

The third-party data source 308*a* may include one or more data sources provided by a third-party system. Such third-party data may include data that is not provided by a subject matter expert 309 and that does not correspond to a pre-defined standard. For example, the third-party data source 308*a* may include a content server that provides electronic content items relating to healthcare. This content, which may include any type of digital media (e.g., videos, image, articles, songs, etc.), may be associated with concept nodes of the curated health ontology 301 using the third-party transformer 310*a*. In a particular example, assume that the curated health ontology 301 includes a concept node about the skin condition eczema. The third-party data source 308*a* may include articles about eczema, stock images of eczema, informational videos for treating eczema at home, and any other suitable content relating to this topic. The third-party data transformer 310*a* may be configured to extract the data from the third-party data source 308*a*, transform the data into a format useable by the curated health ontology 301, and add the data to the curated health ontology 301.

The health graph data source 308*b* may include one or more data sources at which may be obtained health graph data (e.g., any relational data structure describing the health care space). In some examples, the health graph data source 308*b* may host data associated with the RxNorm® standard, although other standards of health graphs may also be used. The health graph data source 308*b* may store the data according to RRF file distribution: Rich Release Format used by Unified Medical Language System (UMLS). This file may be available for download from National Library of Medicine (NLM). RRF files may also include RXNCONSO.RRF—UMLS-style Atoms defining names and term types defined either in RxNorm or from other terminologies included in UMLS, RXNREL.RRF—UMLS-style Relationships file defining reciprocal relationships between RxCUIs (RxNorm Concept Unique Identifiers) listed in RXNCONSO.RRF. Examples of how data from the health graph data source 308*b* is used to generate the curated health ontology 301 include defining a concept node for a medication based the following identifiers has_ingredient, ingredient_of, has_tradename, tradename_of, etc. The health graph transformer 310*b* may be configured to extract the data from the health graph data source 308*b*, transform the data into a format useable by the curated health ontology 301, and add the data to the curated health ontology 301.

The terminology data 308*c* may include one or more data sources at which may be obtained terminology health data (e.g., any suitable listing of health codes, which do not semantically model content). In some examples, the terminology data source 308*c* may host data associated with the CVX standard. In some examples, a different terminology data source 308*a* may host data associated with the LOINC standard. Although other standards of health terminologies may also be used.

The CVX standard is maintained by National Center of Immunization and Respiratory Diseases (NCIRD) at the Centers for Disease Control CDC), and is available for download at the CDC's website. The CVX standard may include a flat terminology file detailing information about vaccines such as code short name, long name, status, notes, and other suitable information.

The LOINC standard is curated and distributed by Regenstrief Institute and is for download at loinc.org. The LOINC standard may include a .csv file and accessory files. The .csv file (e.g., "loinc.csv") may container a list of LOINC codes defined by combination of six parts: Component/Analyte, System, Time Aspect, Scale Type, Property, and Method Type. In some examples, the file also includes alternate names, auditing data, and unstructured notes about intended use. The accessory files may include GroupsFiles (e.g., associations between LOINC codes based on clinical similarity, conversions between molar and mass quantities), PartsFiles (e.g., additional description of the Parts, with some mappings to other terminologies (including SNOMED CT)), and Expressions file: collaboration with SNOMED CT formally modeling ~22000 LOINC codes according to the SNOMED Observables model). The terminology transformer 310*c* may be configured to extract the data from the terminology data source 308*c*, transform the data into a format useable by the curated health ontology 301, and add the data to the curated health ontology 301.

The ontology data 308*d* may include one or more data sources at which may be obtained ontology health data (e.g., a health graph subject to semantic rules of Web Ontology Language (OWL)). For example, the ontology data 308*d* may include additional SNOMED ontology data. The ontology transformer 310*d* may be configured to extract the data from the ontology data source 308*d*, transform the data into a format useable by the curated health ontology 301, and add the data to the curated health ontology 301.

The other data 308N may include one or more data sources at which may be obtained data other than the third-party data, health graph data, terminology data, or ontology data as described herein. The other transformer 310N may be configured to extract the data from the other data source 308N, transform the data into a format useable by the curated health ontology 301, and add the data to the curated health ontology 301. In some examples, the other data 308N may include data sources that may be added to the system 300 in the future. Such sources may include, for example, ICD-9, ICD-10, ICD-11: International Classification of Diseases, from the World Health Organization (WHO). NDC: National Drug Code directory, maintained by the Food and Drug Administration (FDA), NDFRT: National Drug File—Reference Terminology, maintained by the U.S. Department of Veterans Affairs (VA), UNII: Unique Ingredient Identifier, maintained by FDA, CPT: Current Procedural Terminology, maintained by the American Medical Association (AMA), HCPCS: Healthcare Common Procedure Coding System. For HCPCS, Level I includes CPT, Level II includes general medical services, maintained by AMA.

The subject matter experts 309 may include users who are familiar with clinical health subject matter. Generally, the subject matter experts 309 may review and/or validate aspects of the curated health ontology 301 to confirm that these aspects are clinically relevant and clinically accurate. Thus, while the external data sources 308 may be data files, the subject matter experts 309 are actual people who can subjectively review the curated health ontology 301 and suggest changes. In some examples, the SME transformer 310e is used to transform suggested changes.

The subject matter experts 309 may use one or more user devices to interact with the ontology management system 104 to augment the curated health ontology 301. In some examples, the subject matter experts 309 use an interface such as a user interface or an API to interact with the ontology management system 104. The SME transformer 310e may be configured to extract the data input by the subject matter experts 309, transform the data into a format useable by the curated health ontology 301, and add the data to the curated health ontology 301.

In a particular example, the SME transformer 310e may function as described below. To begin, the SME transformer 310e may receive an SME import file from the subject matter expert 309. Next the SME transformer 310e perform an extraction step which includes, for example, reading group/series concepts and proposed card-friendly names from the SME import file. Next, the SME transformer 310e may perform a transforming step which includes, for example, finding all primary concepts mapped by reference terminology codes specified in file (e.g., identify all LOINC codes) and adding or updating card-friendly names as specified by subject matter experts 309, finding or creating all concept room and series concepts specified by the subject matter experts 309 and adding or updating on room and series concepts, and adding or updating relationships (e.g., primary concept "grouped by" room concept, primary concept "charted with" series concept, and series concept "is a" room concept).

The ontology management engine 220 also includes a validation engine 312. The validation engine 312 may be configured to validate aspects of the health ontology 301. This may include validating that these aspects are clinically relevant and clinically accurate, among other things.

The ontology management system 104 also includes the sub-ontology generation engine 222. The sub-ontology generation engine 222 takes as input a set of selection criteria from one of the requesting systems 302 (or some other device or system associated with the requesting system 302 (e.g., a consuming system)), parses the selection criteria to identify a set of concepts from the curated health ontology 301, and builds a sub-ontology that includes the identified set of concepts. This sub-ontology is then provided to the requesting system 302 for use in saving, organizing, and presenting health record data on the requesting system 302. Examples of requesting systems 302 include user devices such as the user device 108, web-based applications, stand-alone applications, electronic health record systems, artificial intelligence voice assistants, and other such similar systems.

FIG. 4 illustrates a diagram showing an example curated health ontology 400 for storing relationships and attributes of a health concept, according to at least one example. The curated health ontology 400 is an example of the curated health ontology 301. The curated health ontology 400 is an example of an ontology that may be generated by the ontology management system 104. An unbroken line between nodes defines a hierarchical relationship, a long dashed line represents a defining relationship, and a short dashed line represents an attribute.

The curated health ontology 400 semantically represents a product that is metFORMIN hydrochloride 850 mg Oral Tablet, a type of medication. The nodes, attributes, and relationships of the curated health ontology 400 may have been sourced from any one or more of the external data sources 308, the standard ontology data 306, and/or the subject matter experts 309.

Turning now to the details of the curated health ontology 400, the curated health ontology 400 includes a node 402 that includes attributes that define an RxNorm code 404 and RxNorm term type (TTY), a preferred name 406, and a synonym 409. The node 402 is connected to a node 408 via an "is a" hierarchical relationship link. The RxNorm TTY is used to indicate generic and branded drug names at different levels of specificity. The node 408 (metFORMIN hydrochloride 850 mg Oral Tablet) includes attribute 410 that defines an RxNorm code and RxNorm TTY. In this example, the RxNorm TTY represented are SBD (semantic branded drug), SCD (semantic clinical drug), SCDC (semantic clinical drug component), PIN (precise ingredient), and IN (ingredient). Other TTYs may also be used.

The node 408 is connected to a node 412 (oral tablet) via an "has_dose_form" defining relationship link. The node 412 is connected to a node 414 (does form) via an "is a" hierarchical relationship link. The node 408 is also connected to a node 416 (Glucament) via an "has_tradename" defining relationship link. The node 416 is connected to a node 418 (trade name) via an "is a" hierarchical relationship link.

The node 408 is also connected to a node 420 (metFORMIN hydrochloride 850 mg) via an "is a" hierarchical relationship link. The node 420 includes an attribute 422 that defines an RxNorm code and RxNorm TTY. The node 420 is also connected to a node 424 (850 mg) via an "has_strength" defining relationship link. The node 424 is connected to a node 426 (strength) via an "is a" hierarchical relationship link. The node 420 is also connected to a node 428 (Metformin hydrochloride) via an "has_active_ingredient" defining relationship link. The node 428 is connected to a node 430 via an "is_modification_of" defining relationship link. The node 428 is also connected to a node 432 (substance) via an "is a" hierarchical relationship link.

The node 420 is also connected to a node 434 (met FORMIN hydrochloride) via an "is a" hierarchical relationship link. The node 434 includes attribute 436 that defines an RxNorm code and RxNorm TTY. The node 434 is also connected to the node 428 via an "has_active_ingredient" defining relationship link.

The node 434 is also connected to a node 438 (product) via an "is a" hierarchical relationship link. The node 438 is connected to a node 442 (metFORMIN) via an "is a" hierarchical relationship link. The node 442 includes attribute 440 that defines an RxNorm code and an RxNorm TTY. The node 442 is also connected to the node 430 via an "has_active_ingredient" defining relationship link.

Figure 5:
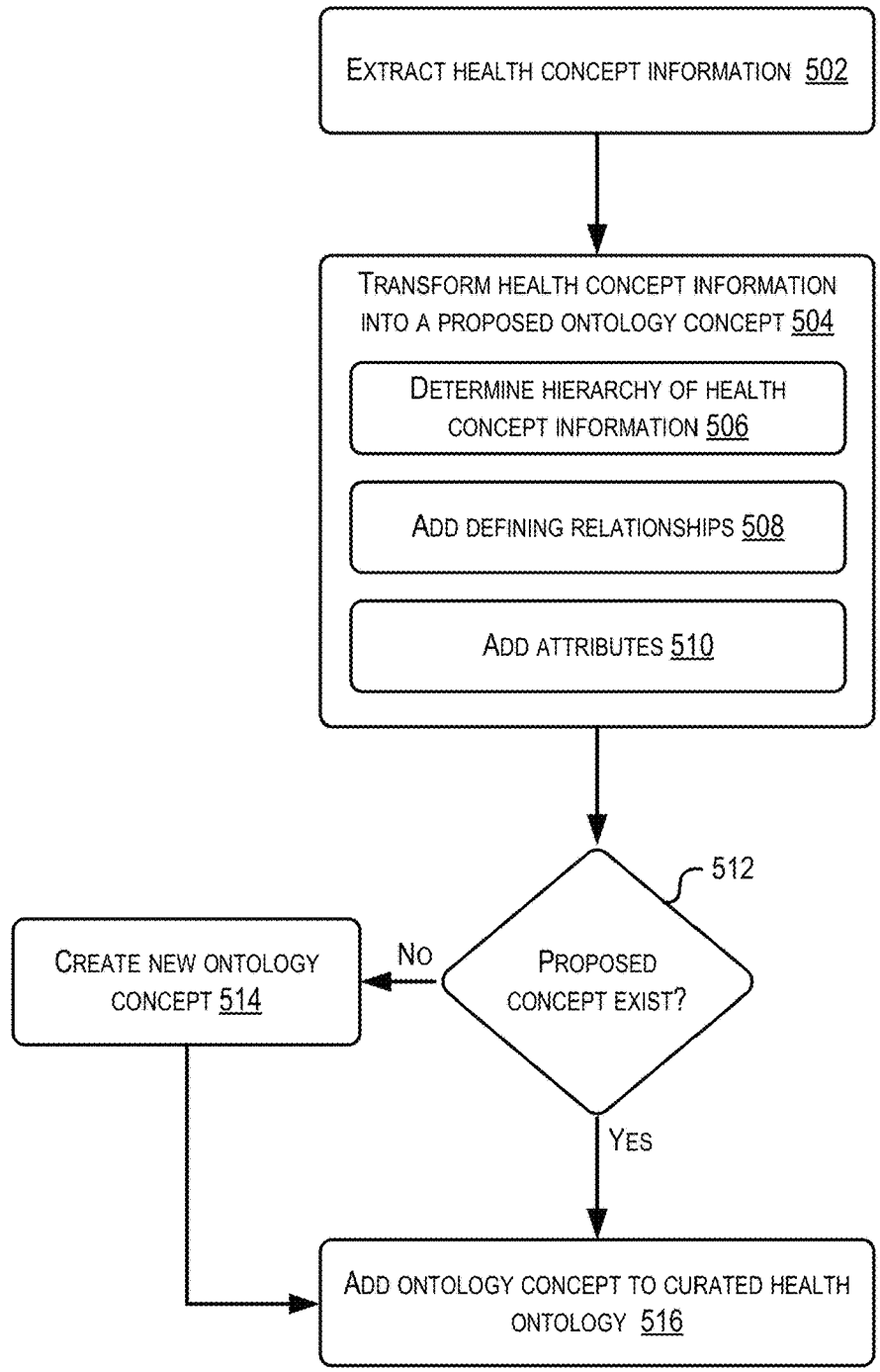
FIG. 5 illustrates a flow chart showing an example process for generating a curated health ontology, according to at least one example.

FIG. 5 illustrates a flow chart showing an example process 500 for generating a curated health ontology, according to at least one example. The process 500 may be performed by the ontology management engine 220 (FIG. 2) of the ontology management system 104 (FIG. 1). The process 500 relates to a process performed by the health graph transformer 310b on data from the health graph data source 308b. In particular, the process 500 includes converting RxNorm semantic modeling into a medicinal product by at least extracting, transforming, and loading data from the health graph data source 308b to form a portion of the curated health ontology 400. While this process is described with respect to the health graph data source 308b, similar blocks may be performed with respect to extracting, transforming, and loading data from any one of the other sources 308 or 309.

The process 500 begins at 502 by the ontology management engine 220 extracting health concept information from a file obtained from the health graph data source 308b. This may include reading RxNorm concept data into a generic concept-atom-relationship-attribute model (e.g., similar to Unified Medical Language System (UMLS)).

At 504, the process 500 includes the ontology management engine 220 transforming the health concept information into a proposed ontology concept. For purposes of this example, the health concept information that will be transformed and loaded is "Fortamet 500 mg pill." The process of transforming the health concept information can include, at 506, determining a hierarchy of health concept information, at 508, adding defining relationships, and, at 510, adding attributes. In particular, at 506, the process 500 includes determining that Fortamet 500 mg pill is a medication.

At 508, the process 500 in particular includes the ontology management engine 220 defining relationships such as: (i) has active ingredient→Metformin (substance), (ii) has basis of strength substance→Metformin hydrochloride (substance), (iii) has presentation strength numerator→500 (qualifier value), (iv) has presentation strength numerator units→mg (qualifier value), (v) has presentation strength denominator→1 (qualifier value), (vi) has presentation strength denominator units→Pill (dose form), (vii) has manufactured dose form→Tablet (dose form), (viii) has route of administration→Oral (qualifier value), and (ix) has trade name→Fortamet (brand or trade name).

At 510, the process 500 in particular includes the ontology management engine 220 adding attributes such as synonyms from RxNorm, preferred name from RxNorm, and code lookup map from reference standard (e.g., RxNorm to health concept ontology map reference set=861001).

At 512, the process 500 includes the ontology management engine 220 determining whether an existing concept exists in the curated health ontology based at least in part on the defining relationships determined at 508. If a concept does not exist (No), the process 500 proceeds to 514, at which, the process 500 includes the ontology management engine 220 defining a new ontology concept. If the concept does exist (Yes), the process 500 proceeds to 516, at which, the process 500 includes the ontology management engine 220 adding the ontology concept to the curated health ontology.

Figure 6:
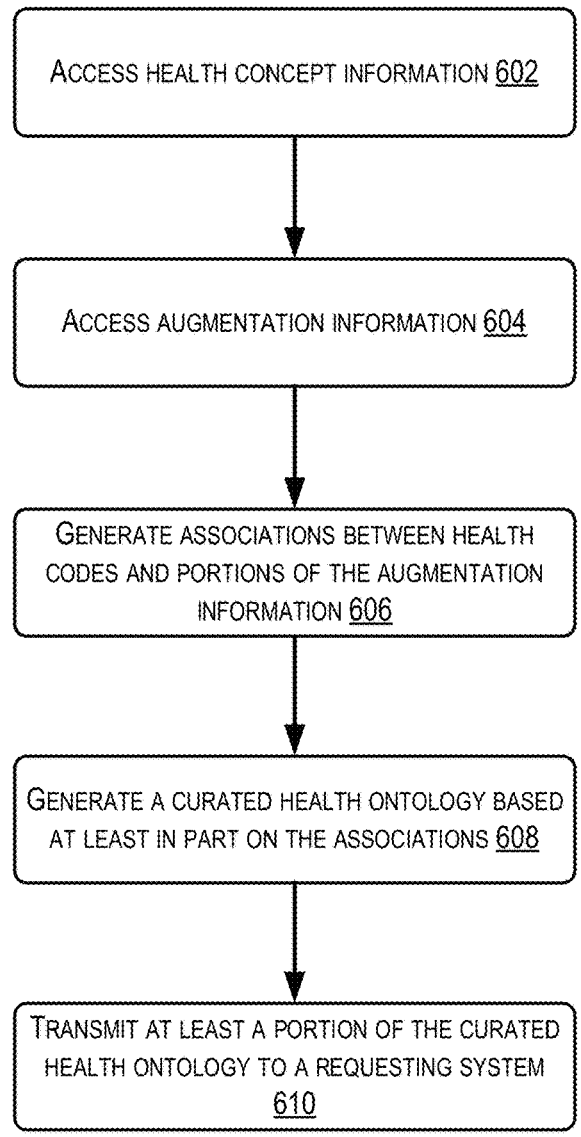
FIG. 6 illustrates a flow chart showing an example process for generating a curated health ontology, according to at least one example.

FIG. 6 illustrates a flow chart showing an example process 600 for generating a curated health ontology, according to at least one example. The process 600 may be performed by the ontology management engine 220 (FIG. 2) of the ontology management system 104 (FIG. 1). The process 600 relates to a generic process for generating a curated health ontology such as the curated health ontology 400.

The process 600 begins at 502 by the ontology management engine 220 accessing health concept information. The health concept information may correspond to a standard health coding ontology, which may include a set of health codes. In some examples, the standard health coding ontology may be based at least in part on the SNOMED® Clinical Terms (CT) standard. In some examples, accessing the health concept information corresponding to the standard health coding ontology may include accessing the health concept information from an ontology server that is configured to support the standard health coding ontology.

At 604, the process 600 includes the ontology management engine 220 accessing augmentation information. The ontology management engine 220 may access the augmentation information from at least one augmentation source. The augmentation information may correspond to at least one health concept. In some examples, the augmentation information may be received from one or more subject matter experts to validate relationships and data in the curated health ontology.

In some examples, the augmentation source may include one or more of a health coding standard, a subject matter expert input interface, or a third-party data source. In some examples, the health coding standard may include at least one of a clinical drug coding standard, a clinical lab results coding standard, a health record transportation coding standard, a vaccine coding standard, or a clinical imaging coding standard. In some examples, the subject matter expert input interface may include a predefined set of communication methods that enables a user to provide a portion of the augmentation information to adjust the curated health ontology. In some examples, accessing the augmentation information may include receiving the augmentation information from the user via the predefined set of communication methods. In some examples, the third-party data sources may include a library of electronic content items.

At 606, the process 600 includes the ontology management engine 220 generating associations between health codes of the set of health codes and portions of the augmentation information. The ontology management engine 220 may generate the associations using one or more transformer engines and based at least in part on the augmentation information. In some examples, at least one transformer engine of the one or more transformer engines may be specific to the type of the augmentation source.

In some examples, generating the associations may include mapping individual health codes of the standard health coding terminology to the individual health codes of the set of health codes of the standard health coding ontology.

In some examples, generating the associations may include mapping individual electronic content items of the library of electronic content items to the individual health codes of the set of health codes of the standard health coding ontology.

In some examples, each concept node of the plurality of concept nodes may represent a particular health concept and may be associated with a portion of the augmentation information. In some examples, at least one concept node of the plurality of concept nodes may include a sub-concept node connected to the at least one concept node via a link. The link may semantically represent the relationship between the at least one concept node and the sub-concept node. In some examples, at least one concept node of the plurality of concept nodes may be associated with a set of attributes that is readable by a processing system.

At 608, the process 600 includes the ontology management engine 220 generating a curated health ontology based at least in part on the associations. The curated health ontology may include a plurality of concept nodes. In some examples, each concept node of the plurality of concept nodes may represent at least one health code of the set of health codes.

At 610, the process 600 includes the ontology management engine 220 transmitting at least a portion of the curated health ontology to a requesting system. The portion may include a sub-ontology and may be transmitted for presentation or storage of health record data by the requesting system.

In some examples, transmitting the portion of the curated health ontology may include receiving a request, from a user device associated with the requesting system, for a curated health sub-ontology. The request may identify a set of selection criteria. In this example, transmitting may further include generating the curated health sub-ontology to include a portion of the plurality of concept nodes based at least in part on the selection criteria. The curated health sub-ontology may include fewer concept nodes than the curated health ontology. In this example, transmitting may further include providing the curated health sub-ontology to the user device. In some examples, the anonymized hashing operation described herein may be used to selectively download portions of the curated health ontology.

In some examples, the process 600 may further include storing the curated health ontology in a memory on a server device.

Figure 7:
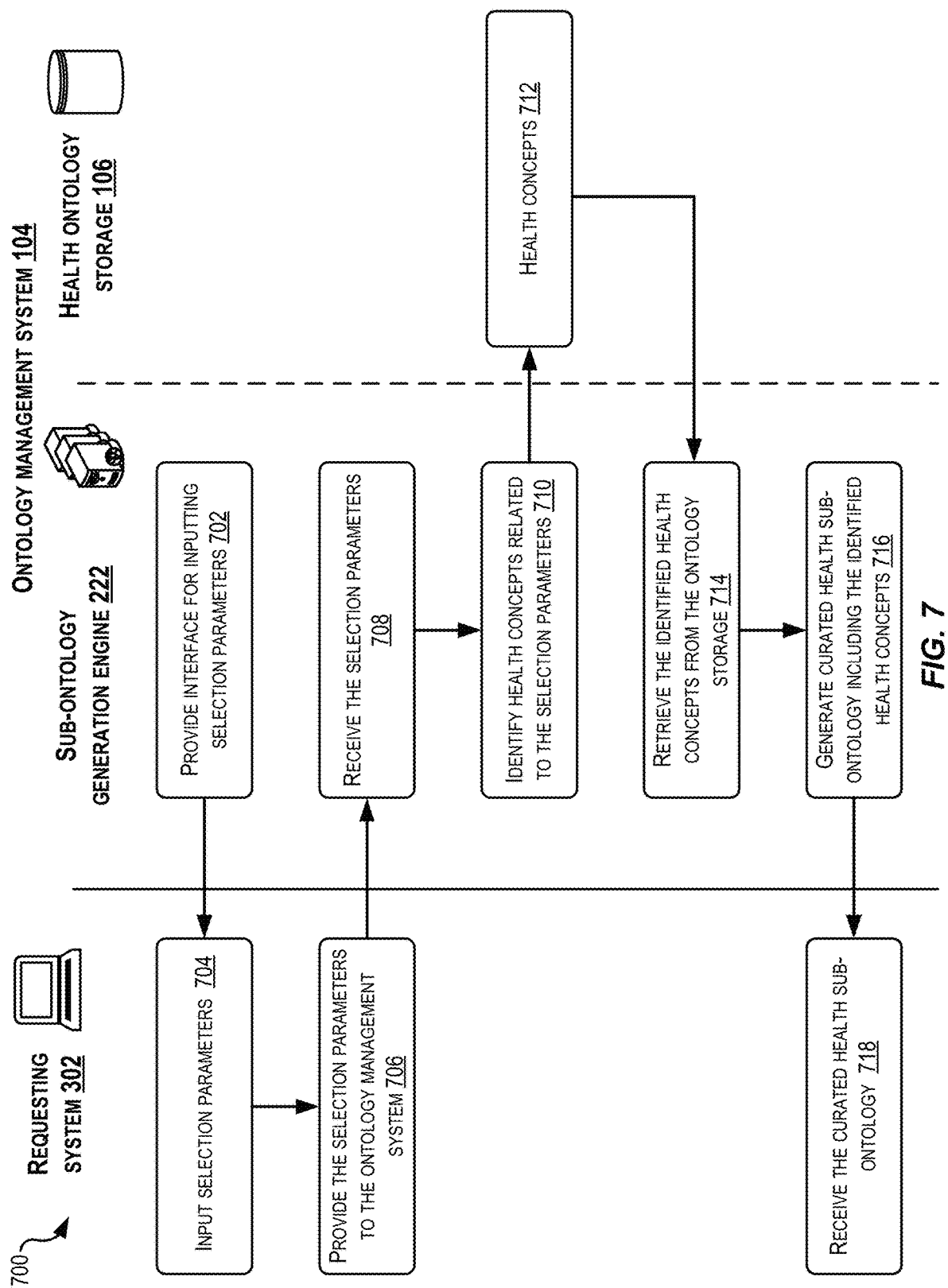
FIG. 7 illustrates a data flow showing an example process for generating a curated health sub-ontology using a curated health ontology, according to at least one example.

FIG. 7 illustrates a data flow showing an example process 700 for generating a curated health sub-ontology using a curated health ontology, according to at least one example. The process 700 may be performed by the requesting system 302 (FIG. 3) and the ontology management system (FIG. 1) including the sub-ontology generation engine 222 (FIG. 2) and the health ontology storage 106 (FIG. 1).

The process 700 begins at 702 by the sub-ontology generation engine 222 providing an interface for inputting selection parameters. This may include the sub-ontology generation engine 222 providing a user interface for presentation at the requesting system 302. The selection parameters may define query parameters for querying the curated health ontology to identify concepts to construct the curated health sub-ontology. The query parameters may be defined by an entry point (e.g., expression which directly queries the ontology and returns a list of concepts), a traversal rule, an attribute type filter (e.g., post-traversal filter on attributes for those concepts found during traversal), and metadata concepts (e.g., concepts required to fully specify required content). The entry point may be, for example, an attribute filter (e.g., reference terminology code lookup), relationship semantics (e.g., descendants of a top-level concept, concepts with "grouped by" relationship, etc.). Traversal rules may include, for example, relationship types (e.g., during graph traversal, which relationships to follow to discover additional concepts) and hierarchy concepts (e.g., those concepts which, if discovered during traversal, should be included in the sub-ontology to supply hierarchical grouping information).

At 704, the process 700 includes the requesting system 302 inputting selection parameters. In some examples, this may include a user manipulating the requesting system 302 to input the selection parameters at the interface provided by the sub-ontology generating engine 222 at 702. The selection parameters may correspond to at least some characteristics of the sub-ontology required by the requesting system 302.

At 706, the process 700 includes the requesting system 302 providing the selection parameters to the ontology management system 104. In some examples, the may include sending the selection parameters via the interface provided by the sub-ontology generation engine 222.

At 708, the process 700 includes the sub-ontology generation engine 222 receiving the selection parameters from the requesting system 302.

At 710, the process 700 includes the sub-ontology generation engine 222 identifying health concepts related to the selection parameters. This may include the sub-ontology generation engine 222 traversing concept nodes of the curated health ontology and forming a list of concept nodes to be copied to the sub-ontology.

At 712, the process 700 includes the sub-ontology generation engine 222 accessing the health concepts in the health ontology storage 106. The health concepts may correspond to the concept nodes.

At 714, the process 700 includes the sub-ontology generation engine 222 retrieving the identified health concepts from the health ontology storage 106. This may include copying the nodes, attributes, and associated nodes corresponding to the identified health concepts.

At 716, the process 700 includes the sub-ontology generation engine 222 generating a health sub-ontology including the identified health concepts. This may include the sub-ontology generation engine 222 combining the identified health concepts and corresponding nodes, links, attributes, and related nodes to the curated health sub-ontology.

At 718, the process 700 includes the requesting system 302 receiving the curated health sub-ontology from the ontology management system 104. In some examples, the requesting system 302 is then enabled to use the curated sub-ontology for the presentation of, querying of, and organization of health record data.

Figure 8:
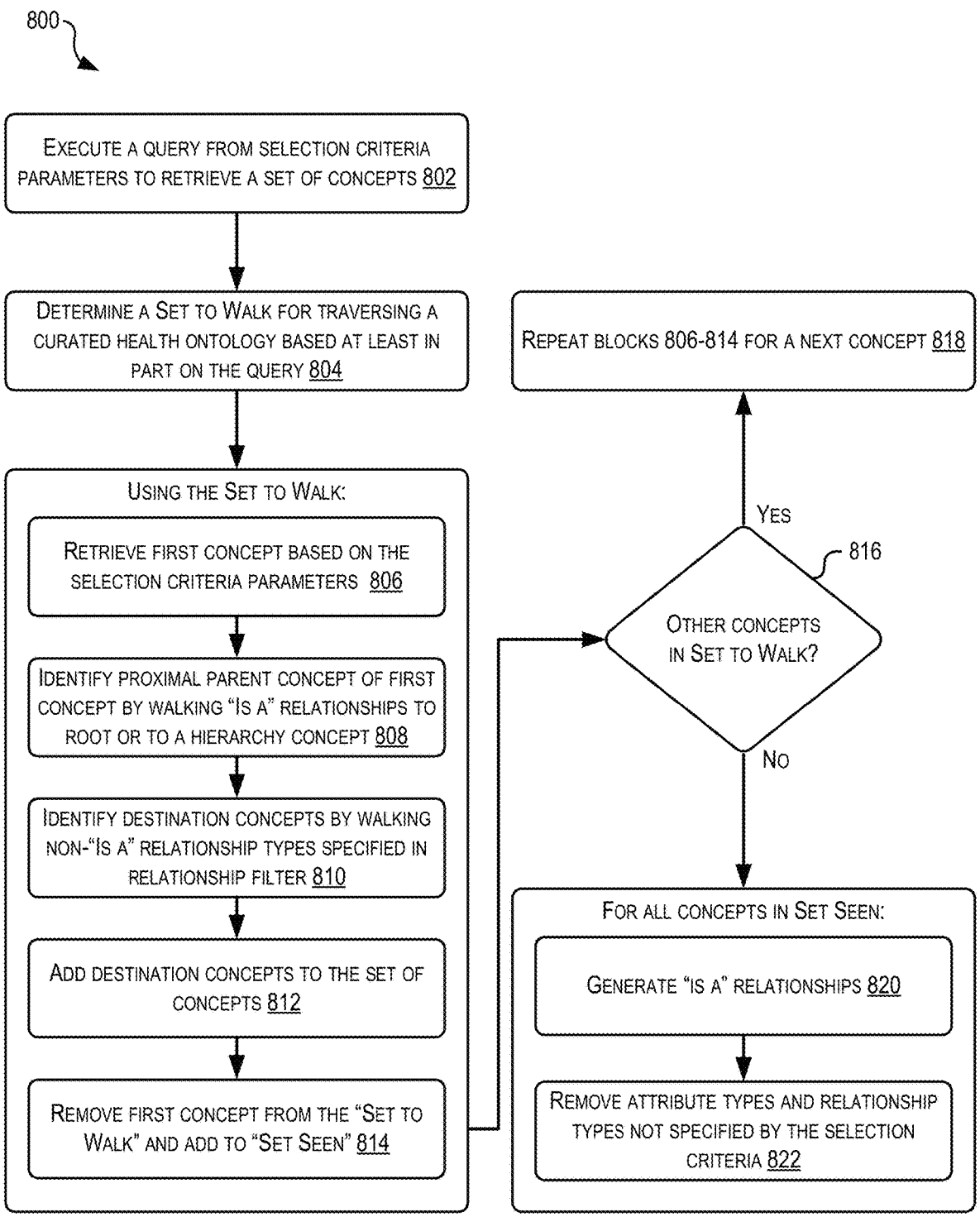
FIG. 8 illustrates a flow chart showing an example process for generating a curated health sub-ontology, according to at least one example.

FIG. 8 illustrates a flow chart showing an example process for generating a curated health sub-ontology, according to at least one example. The process 800 may be performed by the sub-ontology generation engine 222 (FIG. 2) of the ontology management system 104 (FIG. 1). The process 800 relates to a process performed by the sub-ontology generation engine 222 to generate a sub-ontology for a consuming system. The entry point, traversal rules, attribute filter, and metadata concepts may be adjusted to generate sub-ontologies specific for consuming systems.

The process 800 begins at 802 by the sub-ontology generation engine 222 executing a query from selection criteria parameters to retrieve a set of concepts. The selection criteria parameters may have been received from a requesting system. For example, if the requesting system had requested a sub-ontology for a user device such as the user device 108, the set of concepts may include a set of RxNorm codes, a set of LOINC codes, a set of CVX codes, and a set of FHIR ValueSet concepts. In some examples, the set of concepts may be pages from the ontology and the selection criteria may identify the pages based on a mapping of the concepts in the health record data with the pages in the ontology. If the requesting system had requested a sub-ontology for a specialized EHR system, the set of concepts may include descendants of a set of FHIR ValueSet concepts. In some examples, prior to performing block 802, the process 800 may include the sub-ontology generation engine 222 creating a dummy root concept that will be the basis for the curated health sub-ontology.

As described herein, nodes of the sub-ontology on the user device may include annotations, e.g., metadata or other data that describes aspects of the node, which may be unique to the user. The annotations may be made by the user of the user device 108 using a user interface, generated in an automated manner based on a set of heuristics, and/or created in any other suitable manner (e.g., probabilistic).

In addition to or instead of retrieving the set of concepts, the process 800 may also include, in some examples, querying nodes (including annotations) of the sub-ontology given a set of queries. For example, a set of queries may define that the user has a certain medical condition associated with high blood pressure and that the user has had high blood pressure over the last six months, and the querying may return information about these two queries.

At 804, the process 800 includes the sub-ontology generation engine 222 determining "a set to walk" for traversing a curated health ontology based at least in part on the query. The "set to walk" is essentially a set of concepts that will be traversed in the curated health ontology to identify nodes to be included in the sub-ontology.

At 806, the process 800 includes the sub-ontology generation engine 222 using the set to walk to retrieve a first concept based on the selection criteria. The first concept may be the first concept from the set to walk.

At 808, the process 800 includes the sub-ontology generation engine 222 using the set to walk to identify proximal parent concepts of the first concept by walking "is a" relationships to root and/or to a hierarchy concept.

At 810, the process 800 includes the sub-ontology generation engine 222 using the set to walk to identify destination concepts by walking non-"is a" relationship types specified in relationship filter (e.g., defining relationships).

At 812, the process 800 includes the sub-ontology generation engine 222 using the set to walk to add destination concepts to the set of concepts.

At 814, the process 800 includes the sub-ontology generation engine 222 using the set to walk to remove the first concept from the "set to walk" and add to "set seen."

At 816, the process 800 includes the sub-ontology generation engine 222 determining whether there are other concepts in the "set to walk." In some examples, this may include accessing the set to walk to identify if any additional concepts are available. If other concepts exist (Yes), at 818, the process 800 includes the sub-ontology generation engine 222 repeating blocks 806-814 for the next concept.

Function of the blocks 806-814 may be defined by the traversal rules for a given consuming system. For example, if the requesting system had requested a sub-ontology for a user device such as the user device 108, the traversal rules may have included relationship type rules (e.g., "Grouped by", to include grouping information curated by the subject matter experts 309, "Charted with", to include charting information curated by the subject matter experts 309, "Is a"←restricted to hierarchy concept chains) and hierarchy concepts (e.g., FHIR ValueSet concepts, "CHR Labs", "CHR Medications", and "CHR Immunizations"). If the requesting system had requested a sub-ontology for a specialized EHR system, the traversal rules may have included relationship type rules (e.g., "is a") and hierarchy concepts (e.g., all FHIR ValueSet concepts).

If other concepts do not exist (No), at 820, the process 800 includes the sub-ontology generation engine 222, for all concepts in "set seen," generating an "is a" relationship. At 822, the process 800 includes, for all concepts in "set seen," the sub-ontology generation engine 222 removing attribute types and relationship types not specified by the selection criteria.

Function of the blocks 820 and 822 may be defined by the attribute type filter for a given consuming system. For example, if the requesting system had requested a sub-ontology for a user device such as the user device 108, the attribute type filter may have included one or more of the following: "RxNorm to curated health ontology simple map reference set," "LOINC to curated health ontology simple map reference set," "CVX to curated health ontology simple map reference set," all FHIR ValueSet code lookup maps, "Nebulous concept" (e.g., used to specify device behavior to ignore vague or meaningless codes), "Hides out-of-range filter" (e.g., used to specify device behavior when charting content where reference ranges should not be displayed), and "Charts blood pressure" (e.g., used to chart special-case device behavior when charting blood pressure). If the requesting system had requested a sub-ontology for a specialized EHR system, the attribute type filter may have included at least the following filter: "Has specialized EHR system simple map to reference set."

Figure 9:
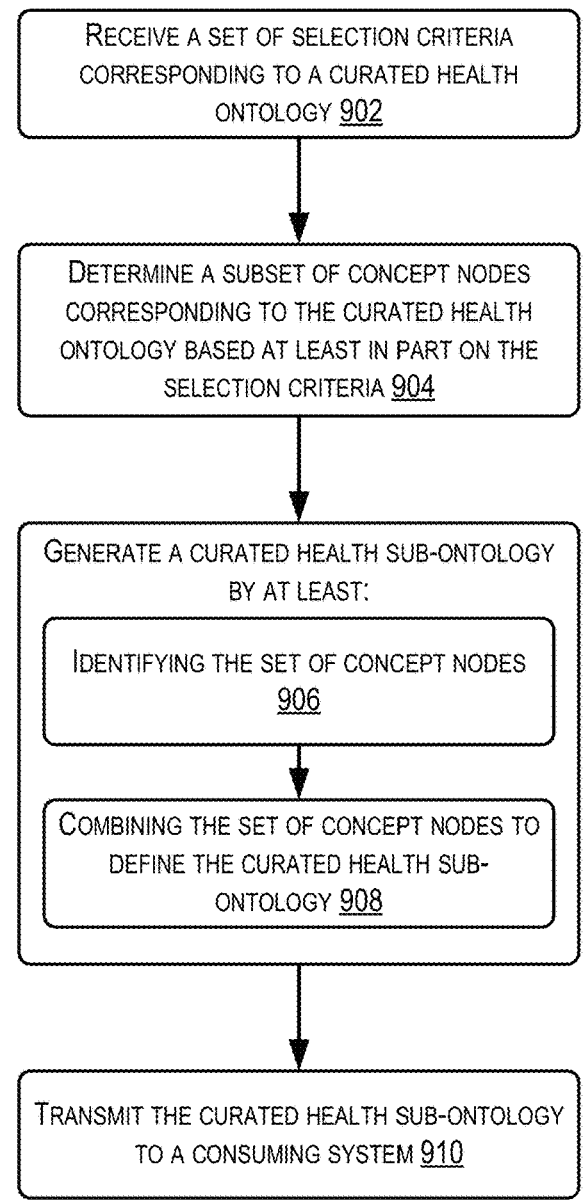
FIG. 9 illustrates a flow chart showing an example process for generating a curated health sub-ontology, according to at least one example.

FIG. 9 illustrates a flow chart showing an example process 900 for generating a curated health sub-ontology, according to at least one example. The process 900 may be performed by the sub-ontology generation engine 222 (FIG. 2) of the ontology management system 104 (FIG. 1). The process 900 relates to a generic process for generating a curated health sub-ontology based on a set of selection parameters.

The process 900 begins at 902 by the sub-ontology generation engine 222 receiving a set of selection criteria corresponding to a curated health ontology. The curated health ontology may include a plurality of concept nodes each representing a health concept. In some examples, the set of selection criteria may define a set of query parameters for querying the curated health ontology. In some examples, the set of query parameters may include at least one of an entry point parameter for querying the curated health ontology and obtaining a list of concepts corresponding to a portion of the concept nodes, a traversal rule for defining traversal paths for traversing the curated health ontology, an attribute type filter for filtering concepts based on attributes, or a metadata concept rule that defines requested metadata for the curated health sub-ontology. In some examples, the entry point parameter may include an attribute filter that references a terminology code lookup table associated with a standard health coding terminology. In some examples, the traversal rule may include at least one of a relationship type traversal rule that defines the traversal paths with respect to relationships between concept nodes or a hierarchy concept traversal rule that defines which hierarchal concept nodes, when discovered, along the traversal paths will be included in the curated health sub-ontology. In some examples, the set of selection criteria may be specified in the curated health ontology.

At 904, the process 900 includes the sub-ontology generation engine 222 determining a subset of concept nodes corresponding to the curated health ontology based at least in part on the set of selection criteria. This may include determining a set to walk to determine which nodes will be traversed to include in the sub-ontology. In some examples, determining the set of concept nodes includes may include executing a query based at least in part on the selection criteria to retrieve a list of concepts represented by the set of concept nodes.

At 906, the process 900 includes the sub-ontology generation engine 222 generating a curated health sub-ontology by at least identifying the set of concepts from the curated health ontology. In some examples, the curated health ontology may be based at least in part on a standard health ontology including a set of health codes and a standard health coding terminology. In some examples, the standard health coding ontology may be based at least in part on the SNOMED® Clinical Terms (CT) standard. In some examples, the standard health coding terminology may include at least one of a clinical drug coding standard, a clinical lab results coding standard, a health record transportation coding standard, a vaccine coding standard, or a clinical imaging coding standard.

In some examples, identifying the set of concept nodes may include iteratively repeating for each concept of the list of concepts, retrieving a concept of the list of concepts, and traversing the curated health ontology to identify a subset of concept nodes of the set of concept nodes. The subset of concept nodes may relate to the concept.

At 908, the process 900 includes the sub-ontology generation engine 222 generating the curated health sub-ontology by at least combining the set of concepts nodes to define the curated health sub-ontology. In some examples, at least one concept node of the set of concept nodes may include a sub-concept node connected to the at least one concept node via a link. The link may semantically represent the relationship between the at least one concept node and the sub-concept node. In some examples, combining the set of concept nodes may include combining respective subsets of concept nodes identified based at least in part on traversing the curated health ontology.

At 910, the process 900 includes the sub-ontology generation engine 222 transmitting the curated health sub-ontology to a consuming system. In some examples, the consuming system may include at least one of a handheld user device, an electronic health record (EHR) system, or a virtual assistant. In some examples, transmitting the curated health sub-ontology to the consuming system may include sending the curated health sub-ontology to a user device associated with the consuming system. In some examples, the curated sub-ontology is customized for the consuming system.

In some examples, receiving the set of selection criteria and transmitting the curated health sub-ontology may be performed using a predefined set of communication methods. In some examples, the set of selection criteria may be received from a user device, and transmitting the curated health sub-ontology may include sending the curated health sub-ontology to the user device.

Figure 10:
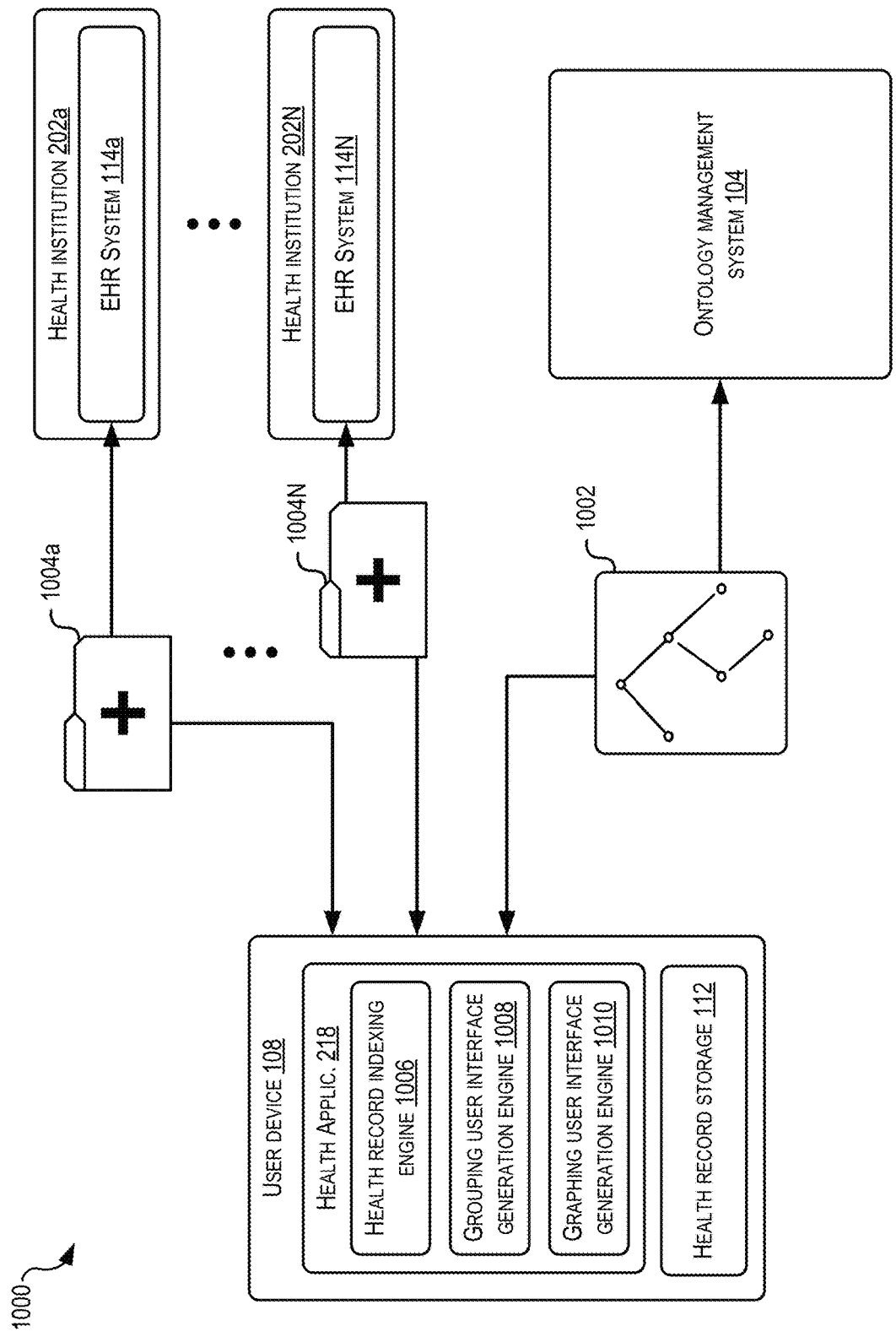
FIG. 10 illustrates a block diagram showing an example system for indexing and storing health record data from multiple health institutions using a curated health sub-ontology, according to at least one example.

FIG. 10 illustrates a block diagram showing an example system 1000 for indexing and storing health record data from multiple health institutions using a curated health sub-ontology 1002, according to at least one example. The system 1000 is a simplified version of the system 200 described with respect to FIG. 2. Thus, the system 1000 includes the user device 108 in network communication with one or more EHR systems 114 of one or more health institutions 202, and in network communication with the ontology management system 104.

While not explicitly illustrated in FIG. 10, the user device 108 typically connects to the EHR systems 114 with the assistance of the provider Web system 204. After the initial connections have been formed, however, the user device 108 may maintain ongoing connections with the EHR systems 114. In this manner, whenever an instance of the electronic health record is updated by one of the EHR systems 114, the user device 108 can obtain the updates. As illustrated, the user device 108 obtains a first instance of the health record 1004*a* from the EHR system 114*a* and a second instance of the health record 1004N from the EHR system 114N. Any suitable number of connections may be made with any suitable number of EHR systems 114 to download any suitable number of instances of the health record 1004.

Additionally, while a direct connection is shown between the ontology management system 104 and the user device 108, it should be understood that the curated health sub-ontology 1002 may be shared with the user device 108 via one or more other system components (not illustrated). For example, the ontology management system 104 may interact with a requesting system, as described in more detail with respect to FIG. 7, and the requesting system may share the curated health sub-ontology 1002 with the user device 108. In some examples, the user device 108 may receive the curated health sub-ontology 1002 from the updater service 209. In some examples, the user device 108 may receive the curated health sub-ontology 1002 directly from the ontology management system 104, e.g., the user device 108 may be considered the requesting system and the consuming system.

As introduced herein, the user device 108 includes the health record storage 112 and the health application 218 including a health record indexing engine 1006, a grouping user interface generation engine 1008, and a graphing user interface generation engine 1010. In some examples, the health record indexing engine 1006, the grouping user interface generation engine 1008, and the graphing user interface generation engine 1010 are each configured to perform particular functions described in further detail with respect to the flowcharts.

Generally, the health record indexing engine 1010 is configured to use the curated health sub-ontology to index health record data obtained from the health records 1004. The health record indexing engine 1010 is also configured to generate an on-device personal health ontology that is unique to the health record data and therefore unique to a user profile of the user device 108 to which the health record data belongs.

Generally, the grouping user interface generation engine 1008 is configured to use the personal health ontology to group items from disparate health records 1004 within one application as part of presenting the grouped items at a display of the user device 108. The grouping may include grouping by category, grouping within a category, and grouping in other ways. The grouping user interface generation engine 1008 may generate a plurality of user interfaces, as described herein, to present health record data.

Generally, the graphing user interface generation engine 1008 is configured to use the personal health ontology to graph items from disparate health records 1004 within one application. The graphed items may be presented in connection with one or more filters for graphically identifying different characteristics of the underlying data.

Figure 11:
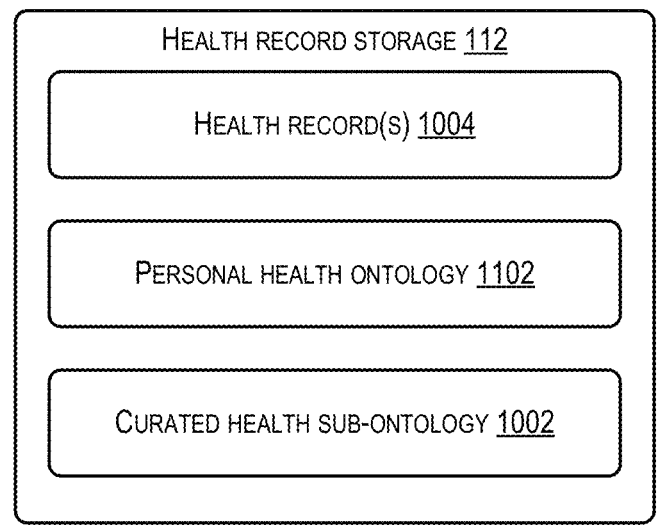
FIG. 11 illustrates a block diagram showing an example device for storing health record data, a curated health sub-ontology, and a personal health ontology on a user device, according to at least one example.

FIG. 11 illustrates a block diagram showing an example device 1100 for storing health record data 1004, the curated health sub-ontology 1002, and a personal health ontology 1102 on a user device, according to at least one example. In some examples, the device 1100 is the health record storage 112 described with reference to earlier figures. The health record storage 112 may include any suitable logical and/or physical divisions such as separate databases, memory modules, and the like to enable storage of the health records 1004, the personal health ontology 1102, and the curated health sub-ontology 1002. In some examples, the personal health ontology 1102 and the curated health sub-ontology 1002 are stored in the same database.

Figure 12:
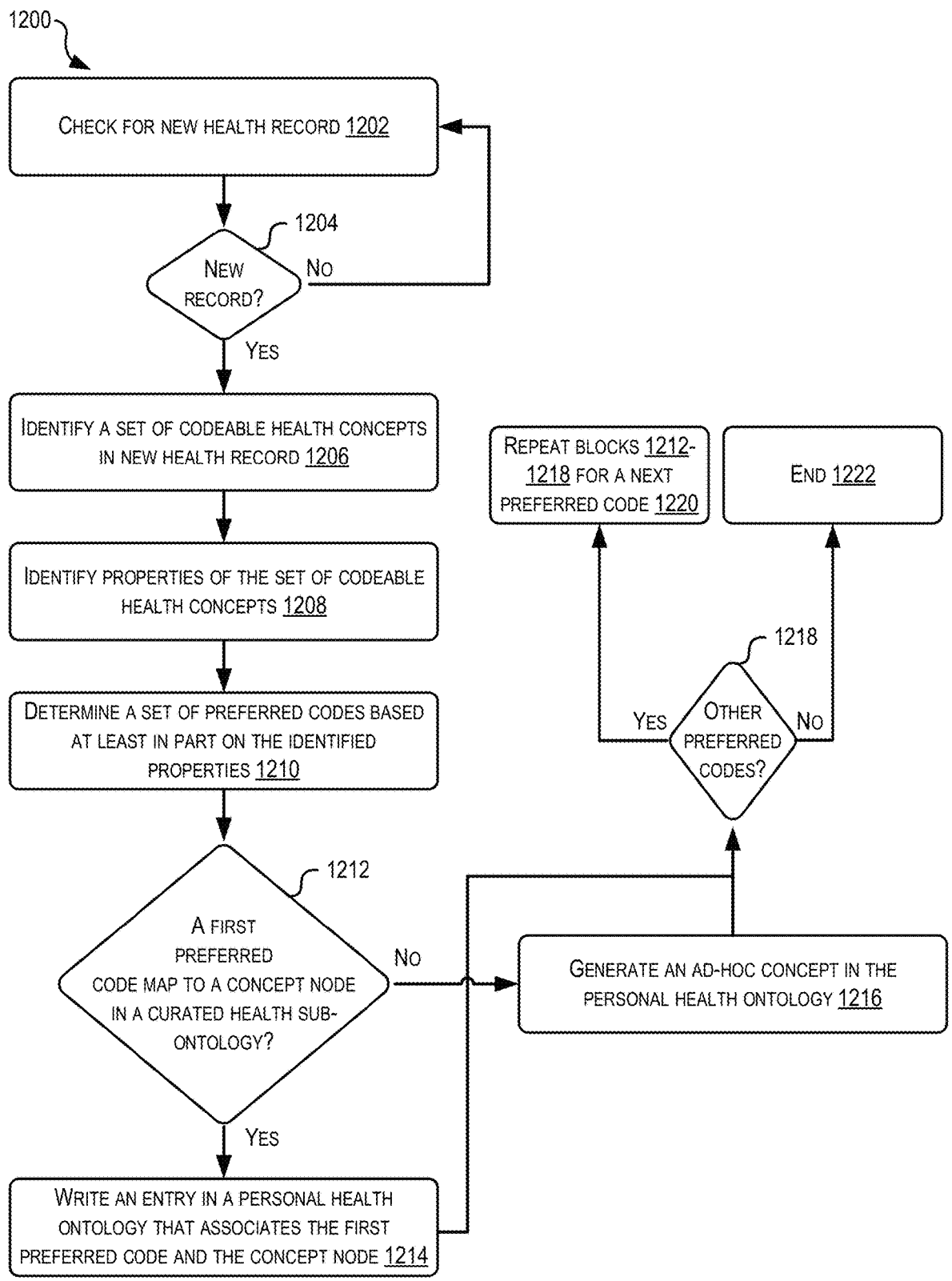
FIG. 12 illustrates a flow chart showing an example process for indexing health record data using a curated health sub-ontology, according to at least one example.

FIG. 12 illustrates a flow chart showing an example process 1200 for indexing health record data using a curated health sub-ontology, according to at least one example. The process 1200 may be performed by the health record indexing engine 1006 (FIG. 10) of the user device 108 (FIG. 10). The process 1200 relates to a process performed by the health record indexing engine 1006 to check for new health records, index health record data for new health records using a curated health sub-ontology, create a personal health ontology based on the indexing, and store the health data and the personal health ontology on the user device 108.

The process 1200 begins at 1202 by the health record indexing engine 1006 checking for a new health record. This may include the health record indexing engine 1006 executing a listener on the user device 108. The listener detects when health record data is downloaded to the user device 108. This may include a user using the user device 108 to connect to an EHR system 114 and to download health record data. The health record data can be downloaded as a FHIR package (e.g., in a JSON format).

At 1204, the process 1200 includes the health record indexing engine 1006 determining whether the health record data is a new record that has not previously been indexed. This may include the health record indexing engine 1006 comparing an identifier of the health record with identifiers for other health records previously downloaded. In some examples, the health record indexing engine 1006 performs a fingerprint analysis of the health record to determine whether the health record is new.

If the health record is not new (No at 1204), the process 1200 returns to 1202, at which, the health record indexing engine 1006 checks for new health records. If the health record is new (Yes at 1204), the process 1200 proceeds to 1206, at which, the health record indexing engine 1006 identifies a set of codeable health concepts in the new health record. A codeable health concept is any item in the health record that is represented by a code. For example, this can include display strings, relationships, properties, and the like. In some examples, at 1206, the health record indexing engine 1006 identifies and/or forms one or more arrays of codeable health concepts. For example, for a particular code that represents an allergy, an array of codes that represent side effects of the allergy may be identified. In some examples, at 1206, the health record indexing engine 1006 identifies the code by parsing the new health record.

At 1208, the process 1200 includes the health record indexing engine 1006 identifying properties of the set of codeable health concepts. In some examples, the properties may be part of the health record or may be accessed from some other file that references the identified codes. In some examples, the properties may be properties of the code itself and not data represented by the code. For example, a property of a code may indicate a standard coding to which the code belongs and other similar data relating to the properties of the code.

At 1210, the process 1200 includes the health record indexing engine 1006 determining a set of preferred codes based at least in part on the identified properties. For example, some health records may be coded using more than one standard coding. When this is the case, at 1210, the health record indexing engine 1006 selects the set of preferred codes from a set of codes prepared according to more than one standard coding. For example, the systems described herein may prefer an RxNorm code over other comparable codes. In some examples, when only one standard coding is used, the preferred code may be the only code in the health record.

At 1212, the process 1200 includes the health record indexing engine 1006 determining whether a first preferred code maps to a concept node in a curated health sub-ontology. The curated health sub-ontology may be stored on the use device 108. In some examples, the determination at 1212 is achieved using a lookup function that looks for the first preferred code in the curated health sub-ontology.

If the first preferred code does map to a concept node in the curated health sub-ontology (Yes at 1212), the process 1200 proceeds to 1214, at which, the health record indexing engine 1006 writes an entry in a personal health ontology (e.g., a graph database) that associates the first preferred code and the concept node. This process creates a new node in the personal health ontology that maps one or more properties of the first preferred code with the concept node. In this way, the personal health ontology becomes specific to the health record of the user of the user device 108. Once the personal health ontology has been generated, it can be used to not only enhance presentation of the health record data, but also can be queried (e.g., Does a user have a certain condition? Is a user taking a certain drug? What procedures has a user undergone? Etc.?) and used to make recommendations and/or suggestions (e.g., contraindicated drugs, do not have this procedure based on these factors, recommend a test or procedure based on other factors, etc.). The personal health ontology is stored on the user device 108 in such a manner that it may be accessed using an API. For example, third-party applications running on the user device 108 (e.g., those other than the health application) may be given access to the personal health ontology via an API that queries the personal health ontology.

If the first preferred code does not map to a concept node in the curated health sub-ontology (No at 1212), the process 1200 proceeds to 1216, at which, the health record indexing engine 1006 generates an ad-hoc concept in the personal health ontology. This may include using the code from the health record data (including a preferred display string) to derive data from the code (e.g., type of item (e.g., medication, lab, vital, etc.)). The ad-hoc concept can be added as a node to the personal health ontology and can include an identifier that the ad-hoc concept is ad-hoc. This is because ad-hoc concepts may be relied upon differently by the user device 108 when it comes to using the personal health ontology to present health record data. For example, the ad-hoc concept may be used for grouping, but may not be used for a different purpose.

Following both 1214 and 1216, the process 1200 proceeds to 1218, at which, the health record indexing engine 1006 determines whether there are other preferred codes in the set of preferred codes determined at 1210. If there is at least one other preferred code (Yes at 1218), the process 1200 proceeds to 1220, at which, the health record indexing engine 1006 repeats blocks 1212-1218 for a next preferred code. If there are no other preferred codes (No at 1218), the process 1200 ends at 1222.

Figure 13:
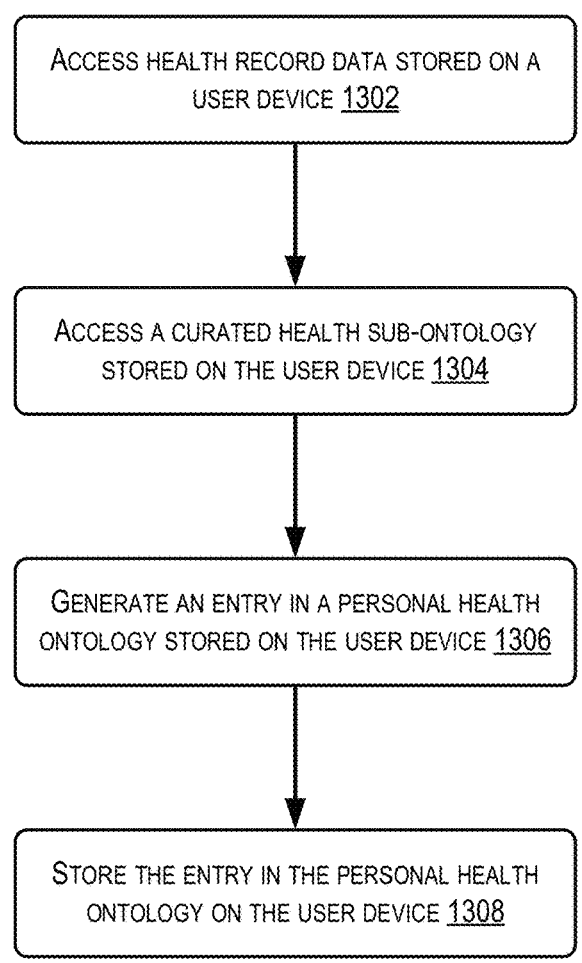
FIG. 13 illustrates a flow chart showing an example process for indexing health record data using a curated health sub-ontology, according to at least one example.

FIG. 13 illustrates a flow chart showing an example process 1300 for indexing health record data using a curated health sub-ontology, according to at least one example. The process 1300 may be performed by the health record indexing engine 1006 (FIG. 10) of the user device 108 (FIG. 10).

The process 1300 begins at 1302 by the health record indexing engine 1006 accessing health record data stored on a user device. The health record data includes a plurality of health record codes corresponding to at least one of a standard health coding ontology or a standard health coding terminology. In some examples, the plurality of health record codes represent a plurality of codeable health concepts. The user device may be a handheld user device such as a mobile phone, a wearable device such as a watch or headset, or any other suitable user device such as a tablet, computer, laptop, etc.

In some examples, the standard health coding ontology may be based at least in part on the SNOMED® Clinical Terms (CT) standard. In some examples, the standard health coding terminology may include at least one of a clinical drug coding standard, a clinical lab results coding standard, a health record transportation coding standard, a vaccine coding standard, or a clinical imaging coding standard.

The health record data may be associated with a user profile corresponding to the user device. The user profile may be associated with a user. The user profile may be for the user to access the user device and associated applications. In some examples, the user device may include multiple user profiles (e.g., a profile for a father and a profile for his son). The health record data can be downloaded to the user device and stored in association with a respective user profile of the multiple user profiles. In some examples, the user profile is associated with multiple healthcare user profiles via the user. For example, the user may maintain multiple healthcare user profiles with multiple health institutions. When the user uses the user device to connect to EHR system of the health institutions, the user may use these other healthcare user profiles for authentication by the EHR systems.

In some examples, accessing the health record data includes accessing first health record data from a first health institution and accessing second health record data from a second health institution. In some examples, the first health record data includes a first instance of a personal electronic health record of a user associated with the user profile, and the second health record data includes a second instance of the personal electronic health record of the user.

In some examples, accessing the health record data from the first health institution includes establishing a secure connection between the user device and a gateway of the first health institution, and downloading, to the user device and via the secure connection, the first instance of the personal electronic health record of the user. The first instance and the second instance may be downloaded as FHIR packages.

At 1304, the process 1300 includes the health record indexing engine 1006 accessing a curated health sub-ontology stored on the user device. The curated health sub-ontology includes a plurality of concept nodes. In some examples, at least one concept node of the plurality of concept nodes may include a sub-concept node connected to the at least one concept node via a link. The link may semantically represent the relationship between the at least one concept node and the sub-concept node. In some examples, the at least one concept node includes one or more annotations that describe one or more attributes of the at least one concept node.

In some examples, the process 1300 may further include, prior to accessing the curated health sub-ontology, downloading the curated health sub-ontology from a server device that hosts a curated health ontology. In some examples, the curated health sub-ontology may include an instance of the curated health ontology. The curated health ontology may include a greater quantity of concept nodes than the plurality of concept nodes of the curated health sub-ontology.

At 1306, the process 1300 includes the health record indexing engine 1006 generating an entry in a personal health ontology stored on the user device. The entry at least associates a health record code of the plurality of health record codes with a concept node of the plurality of concept nodes. In some examples, generating the entry in the personal health ontology may include identifying the health record code based at least in part on accessing the health record data, and matching the health record code to the concept node based at least in part on accessing the curated health sub-ontology.

The personal health ontology may include an index for mapping between the health record data and the curated health sub-ontology. In some examples, the personal health ontology may uniquely represent the health record data. In some examples, the curated health sub-ontology and the personal health ontology may be stored in a database on the user device.

In some examples, the process 1300 may further include generating a different entry in the personal health ontology that at least associates a different health record code of the plurality of health record codes with an ad-hoc health concept. The ad-hoc health concept may be a concept that has not previously associated with the curated health sub-ontology.

At 1308, the process 1300 includes the health record indexing engine 1006 storing the entry in the personal health ontology on the user device.

In some examples, the process 1300 may further include receiving a query corresponding to a health condition of a user associated with the user profile, responsive to the query, generating a response to the query by (i) accessing a particular concept node of the plurality of concept nodes that represents the health condition, (ii) retrieving data associated with the particular concept node, and (iii) generating a response to the query based on the data associated with the particular concept node.

In some examples, the process 1300 may further include evaluating a set of predefined queries by at least traversing the curated health sub-ontology to define a set of relationships between concept nodes of the plurality of concept nodes, and generating a set of entries in the personal health ontology to represent the set of relationships. This is an example of pre-walking the sub-ontology to provide for quick and efficient loading of the content saved in the personal health ontology.

Figure 14:
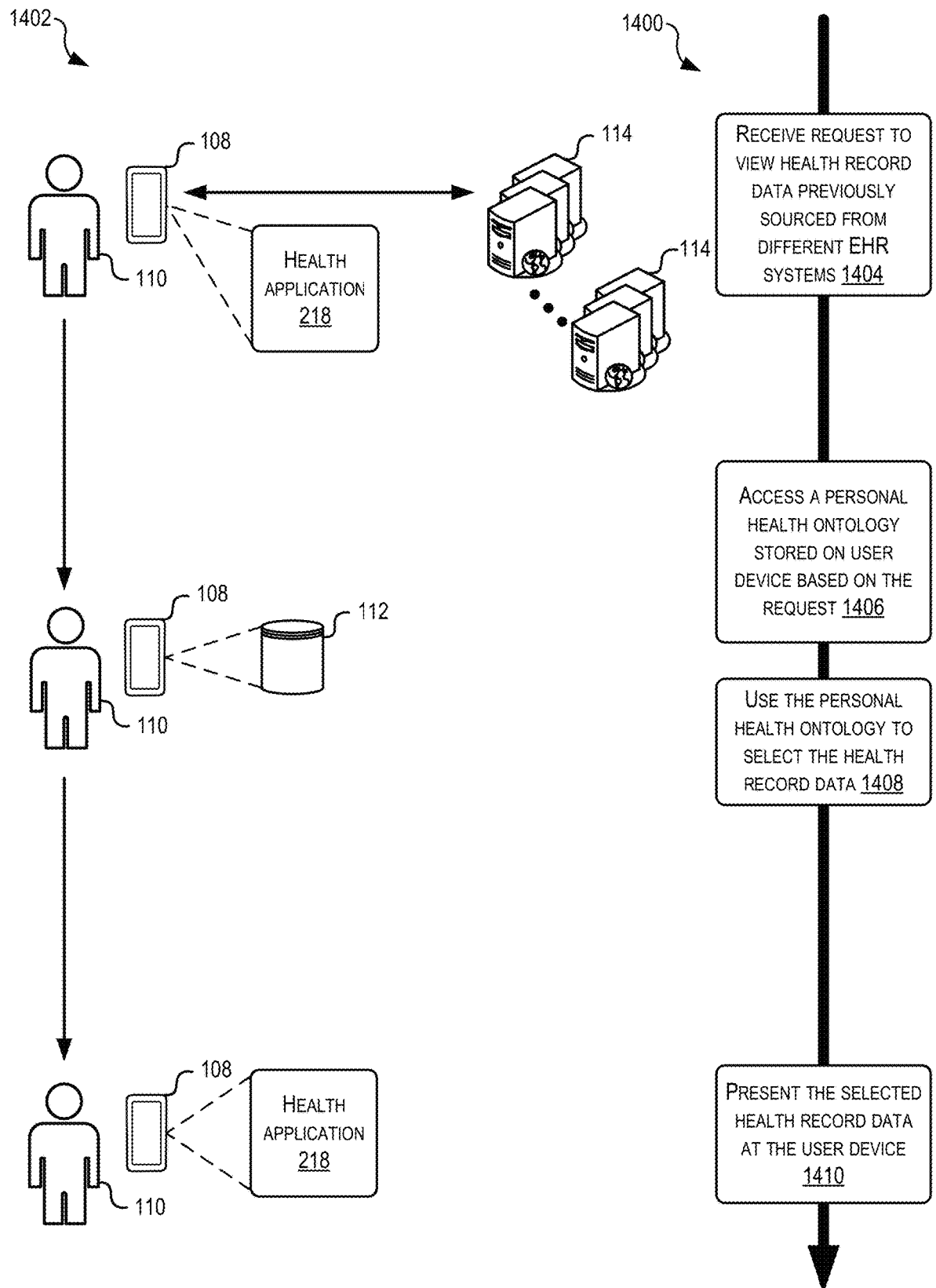
FIG. 14 illustrates a block diagram and a flowchart showing an example process for presenting selected health record data on a user device using a personal health ontology, according to at least one example.

FIG. 14 illustrates a block diagram 1402 and a flowchart showing a process 1400 for presenting selected health record data on a user device using a personal health ontology, according to at least one example. The diagram 102 includes, the user device 108 operated by the user 110, and one or more EHR systems 114*a*-114N.

The process 1400 begins at 1404 by the user device 108 receiving a request to view health record data previously sourced from different EHR systems 114. The request to view may be received via a graphical user interface presented by the health application 218 on the user device. In some examples, the user device 108 previously established connections with the EHR systems 114 to download, index, and store the health record data on the user device 108.

At 1406, the process 1400 includes the user device 108 accessing a personal health ontology stored on the user device 108 based on the request. For example, the request may identify a particular portion of the health record data which may map to one or more nodes of the personal health ontology. As described herein, the personal health ontology may have previously been generated based on an on-device curated health sub-ontology. The personal health ontology may be stored in the health record storage 112 on the user device.

At 1408, the process 1400 includes the user device 108 using the personal health ontology to select the health record data. This may include using the personal health ontology as an index to identify which portions of the health record data are relevant to the request.

At 1410, the process 1400 includes the user device 108 presenting the selected health record data at the user device 108. The selected health record data may be presented via the graphical user interface presented by the health application 218 on the user device 108. In some examples, presenting the selected health record data may include presenting health record data from multiple health institutions in one category or in once concept room.

Figure 15:
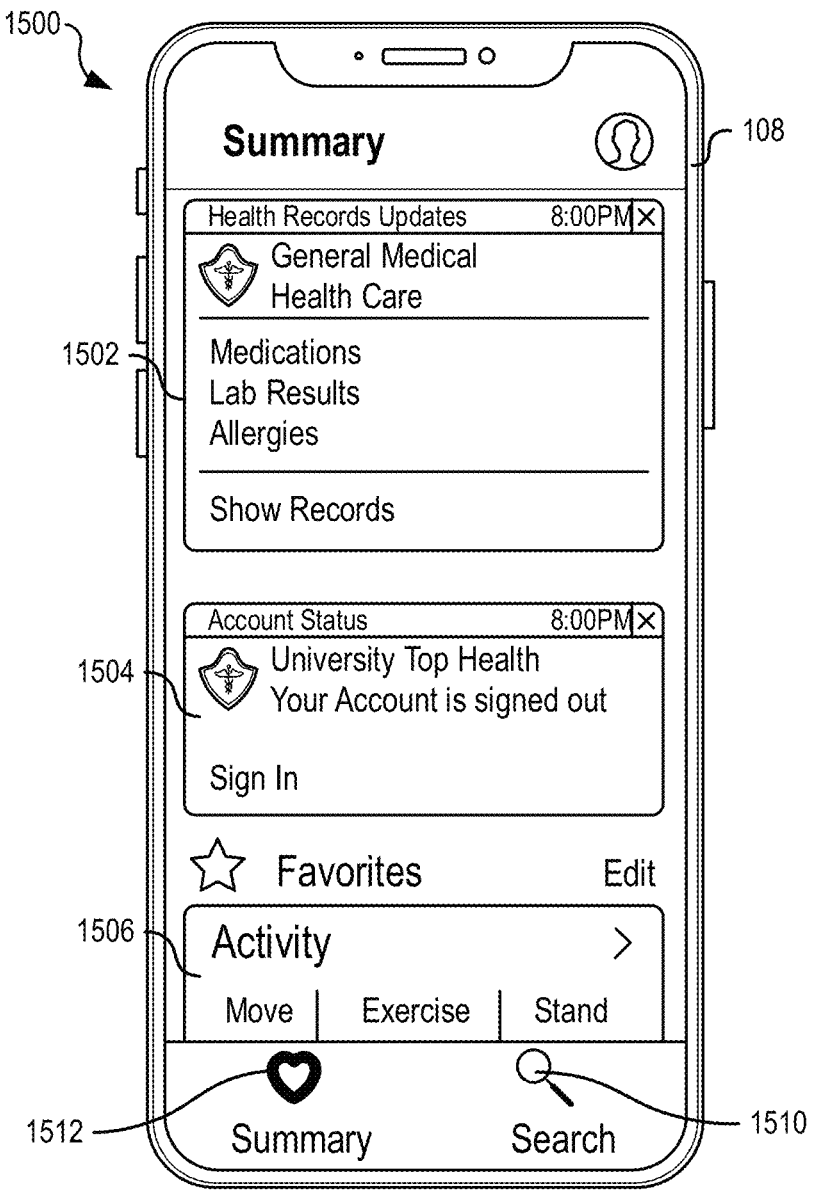
FIG. 15 illustrates a user interface for presenting selected health record data on a user device using a personal health ontology, according to at least one example.

FIG. 15 illustrates the summary user interface 1500 for presenting selected health record data on the user device 108 using a personal health ontology (e.g., the personal health ontology 1102), according to at least one example. The summary user interface 1500 is accessible within a health application (e.g., the health application 218) and illustrated on a display of the user device 108, which is an example of a handheld mobile device. It should be understood, however, that, in some examples, the summary user interface 1500 may be accessible within other applications, which may include web applications, and on displays of other user devices.

The summary user interface 1500 may present a summary of all health-related data stored on the user device 108. This may include health-related data such as sleep data, activity data tracked by sensors of the user device 108 and/or received from a different user device (e.g., a wearable device) 1506, heart rate data, step data showing the number of steps the user has taken over some period of time, a summary of recent updates to the user's health record 1502, account status 1504, and any other suitable summary information. For example, the health record update summary section 1502 may identify which items of the health record data have been updated, an associated health institution (e.g., General Medical Health Care), and an option for showing more records. This data may be presented on one or more user interface cards or with respect to other user interface elements. Selection of the health record update summary section 1502 will cause the device 108 to present a user interface 1600, as illustrated in FIG. 16.

The user interface 1500 also includes a search selector 1510 and a summary selector 1512. Depending on which of the selectors 1510, 1512 is selected, one may be highlighted and/or bolded. Selection of the search selector 1510 will present a search user interface 1800 for searching within the health application, which can be limited to searching the health records stored by the health application. The search user interface is discussed with reference to FIG. 18. Selection of the summary selector will present the summary user interface.

Figure 16:
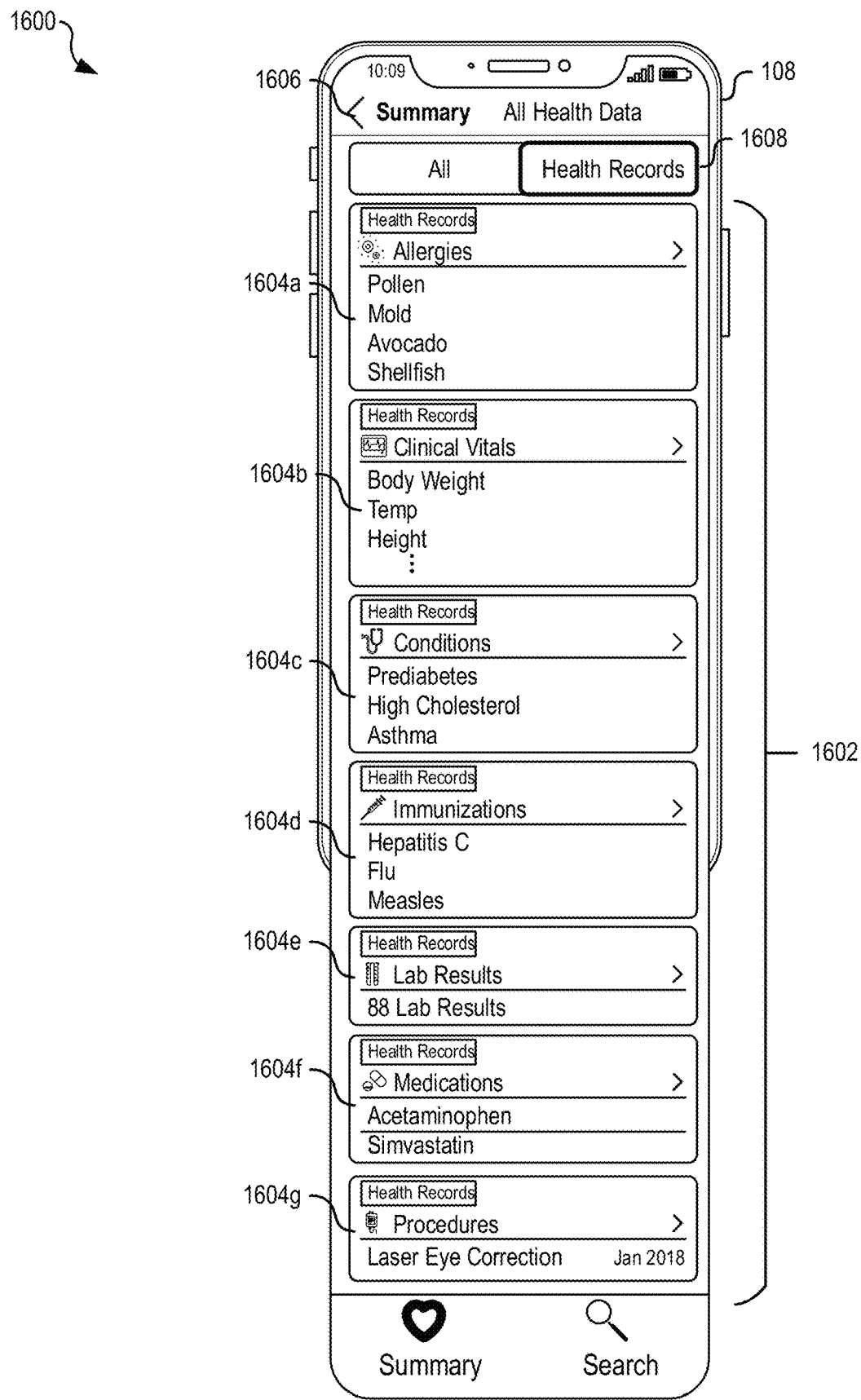
FIG. 16 illustrates a user interface for presenting selected health record data on a user device using a personal health ontology, according to at least one example.

As introduced previously, FIG. 16 illustrates the user interface 1600 for presenting selected health record data on a user device 108 using a personal health ontology (e.g., the personal health ontology 1102), according to at least one example. The user interface 1600 is accessible within a health application (e.g., the health application 218) and illustrated on a display of the user device 108, which is an example of a handheld mobile device. It should be understood, however, that, in some examples, the user interface 1600 may be accessible within other applications, which may include web applications, and on displays of other user devices.

The user interface 1600 includes category section 1602 that includes a plurality of category cards 1604a-1604g, and may be presented after the user has selected "show records" in the health record update summary section 1502 of the summary user interface 1500. Each category card 1604 includes a category header and a preview of a few health record items that have been grouped under the category header. For example, the clinical vitals category card 1604b includes the category header "clinical vitals" and the health record items "body weight," "temp," and "height." The other category cards 1604a (allergies), 1604c (conditions), 1604d (immunizations), 1604e (lab results), 1604f (medications), and 1604g (procedures) also include a respective category header and health record items. In order to present the health record items under a respective category header, the health application may access the personal health ontology to identify associations between the health record items and information in the personal health ontology that represents each category.

Selection of any one of the category cards 1604 may present a detailed view of the category card, as illustrated by a user interface 1700. FIG. 17 illustrates the user interface 1700 for presenting selected health record data on the user device 108 using a personal health ontology (e.g., the personal health ontology 1102), according to at least one example. The user interface 1700 is accessible within a health application (e.g., the health application 218) and illustrated on a display of the user device 108, which is an example of a handheld mobile device. It should be understood, however, that, in some examples, the user interface 1700 may be accessible within other applications, which may include web applications, and on displays of other user devices.

The user interface 1700 includes the category card 1604a for allergies. The personal health ontology may be leveraged to organize the list of allergies in some suitable manner. For example, the list of allergies may be organized by recency, pollen being the most recent and shellfish being the oldest. In some examples, the identified list of allergies may have come from different instances of an electronic health record. For example, a first doctor at a university hospital in Hawaii in 2005 may have identified the shellfish allergy and a different doctor at a local clinic in Seattle in 2018 may have identified the pollen allergy.

Returning to FIG. 16, the user interface 1600 also includes a back arrow 1606, the selection of which will return to the summary user interface. The user interface 1600 also includes a filter section that represents that a "health records" filter 1608 has been selected.

As introduced herein, FIG. 18 illustrates a search user interface 1800 for presenting selected health record data on the user device 108 using a personal health ontology (e.g., the personal health ontology 1102), according to at least one example. The search user interface 1800 is accessible within a health application (e.g., the health application 218) and illustrated on a display of the user device 108, which is an example of a handheld mobile device. It should be understood, however, that, in some examples, the search user interface 1800 may be accessible within other applications, which may include web applications, and on displays of other user devices.

The search user interface 1800 is accessible by selection of the search selector 1510 or any other comparable search selector on any of the user interfaces described herein. The search user interface 1800 includes a search bar 1802 for receiving a text or voice input for searching within the health application. The search user interface 1800 also includes a health category section 1806, a health records section 1808, and a health content section 1810. Selection of any item within any of the sections 1806-1810 may cause the user device to present a user interface relating to the selected item.

The health category section 1806 identifies different categories of "health" data stored on the user device 108. The "health" data in this section 1806 is not derived from health record data. Instead, this data is collected by the user device 108 and associated devices (e.g., a smart watch). The health record data is included within the health records section 1808. The items identified in the health records section 1808 correspond to the category cards 1604 illustrated in FIG. 16. In addition, the health records section 1808 includes items labeled "external" (e.g., outside data) and "unreadable data" (e.g., data that cannot be indexed). The health content section 1810 identifies educational content relating to health and a highlights option for highlighting aspects of the user's health.

A few of the items within the health records section 1808 are labeled. In particular, clinical vitals item 1808a, lab results item 1808*b*, and medications 1808*c* are labeled. In some examples, the clinical vitals and the lab results may be referred to as observable values. Selection of the clinical vitals item 1808*a* causes the user device 108 to present a clinical vital user interface 1900 discussed with reference to FIG. 19. In some examples, the clinical vital user interface 1900 may be accessed using a different sequence of selections. Selection of the medications item 1808*c* causes the user device 108 to present a medication user interface 2200 discussed with reference to FIG. 22. In some examples, the medication user interface 2200 may be accessed using a different sequence of selections. Selection of the lab results item 1808*b* causes the user device 108 to present a lab results user interface 2500 discussed with reference to FIG. 25. In some examples, the lab results user interface 2500 may be accessed using a different sequence of selections.

Beginning first with the clinical vital user interface 1900, FIG. 19 illustrates the clinical vital user interface 1900 for presenting selected health record data on the user device 108 using a personal health ontology (e.g., the personal health ontology 1102), according to at least one example. The clinical vital user interface 1900 is accessible within a health application (e.g., the health application 218) and illustrated on a display of the user device 108, which is an example of a handheld mobile device. It should be understood, however, that, in some examples, the clinical vital user interface 1900 may be accessible within other applications, which may include web applications, and on displays of other user devices.

The clinical vital user interface 1900 includes a filter section that includes a "last updated" filter 1902*a* and an "A to Z" filter 1902*b*. In the clinical vital user interface 1900, the "last updated" filter 1902*a* has been selected. Thus, the data presented in the clinical vitals user interface 1900 includes the most recently updated clinical vitals information. As illustrated in FIG. 19, two record entries 1904*a* and 1904*b* have been populated. The record entry 1904*a* was collected on Apr. 26, 2019 at General Medical Health Care and includes a body temperature and a weight. The record entry 1904*b* was collected on Apr. 22, 2019 at General Medical Health Care and includes a body temperature. The user may continue to scroll within the clinical vitals user interface 1900 to view additional clinical vitals updates.

Selection of the "A to Z" filter 1902*b* in the clinical vitals user interface 1900 causes the user device 108 to present a clinical vitals user interface 2000. FIG. 20 illustrates the clinical vitals user interface 2000 for presenting selected health record data on the user device 108 using a personal health ontology (e.g., the personal health ontology 1102), according to at least one example. The clinical vitals user interface 2000 is accessible within a health application (e.g., the health application 218) and illustrated on a display of the user device 108, which is an example of a handheld mobile device. It should be understood, however, that, in some examples, the clinical vitals user interface 2000 may be accessible within other applications, which may include web applications, and on displays of other user devices.

The clinical vitals user interface 2000 includes an alphabetized clinical vitals list 2002. The items included in the clinical vitals list 2002 represent that actual health record data exists corresponding to the particular item. For example, the health application includes blood pressure records, body temperature records, head circumference records, heart rate records, and height records. As such, these records are represented in the clinical vitals list 2002. The user device 108 may use the personal health ontology to create and present the clinical vitals list 2002. The user may continue to scroll within the clinical vitals user interface 2000 to view additional records for additional clinical vitals.

Selection of any one of the items in the clinical vitals list 2002 cases the user device 108 to present a detailed user interface specific to the subject matter of the selected item. For example, selection of an item 2002*a* relating to body temperature causes the user device 108 to present a clinical vitals user interface 2100 dedicated to body temperature, illustrated in FIG. 21. In some examples, the clinical vitals user interface 2100 is referred to as a concept room because it organizes health record data with respect to a particular concept-body temperature.

Figure 21:
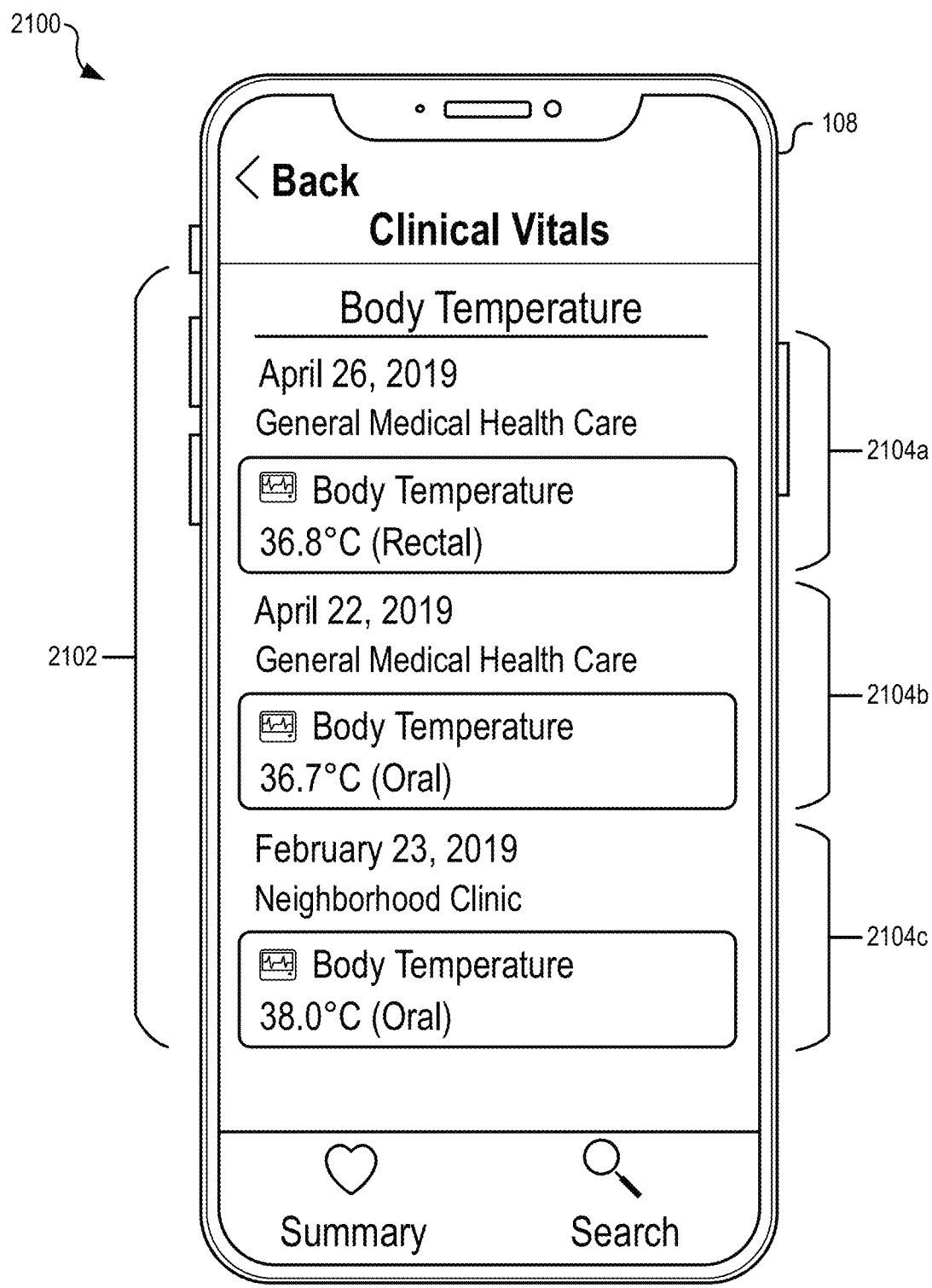
FIG. 21 illustrates a user interface for presenting selected health record data on a user device using a personal health ontology, according to at least one example.

As introduced previously, FIG. 21 illustrates the clinical vitals user interface 2100 for presenting selected health record data on the user device 108 using a personal health ontology (e.g., the personal health ontology 1102), according to at least one example. The clinical vitals user interface 2100 is accessible within a health application (e.g., the health application 218) and illustrated on a display of the user device 108, which is an example of a handheld mobile device. It should be understood, however, that, in some examples, the clinical vitals user interface 2100 may be accessible within other applications, which may include web applications, and on displays of other user devices.

The clinical vitals user interface 2100 includes a record list 2102 including record entries 2104*a*-2104*c*. The record entries 2104 each correspond to a particular event at which a body temperature vital sign measurement was taken and recorded in the health record data. The record entries 2104 may have been recorded in different instances of a user's health record or within the same instance. For example, the record entries 2104*a* and 2104*b* were taken at "General Medical Health Care" and the record entry 2104*c* was taken at "Neighborhood Clinic." In some examples, these two entities may use different EHR systems and/or may code their records using different coding standards. Irrespective of these differences and any other difference in the formatting or coding of the actual health records, the user device 108 may use the personal health ontology, as described herein, to group all record entries relating to body temperature into the record list 2102.

Turning now to the medication user interface 2200, FIG. 22 illustrates the medication user interface 2200 for presenting selected health record data on the user device 108 using a personal health ontology (e.g., the personal health ontology 1102), according to at least one example. The medication user interface 2200 is accessible within a health application (e.g., the health application 218) and illustrated on a display of the user device 108, which is an example of a handheld mobile device. It should be understood, however, that, in some examples, the medication user interface 2200 may be accessible within other applications, which may include web applications, and on displays of other user devices.

The medication user interface 2200 includes a filter section that includes a "last updated" filter 2202*a* and an "A to Z" filter 2202*b*. In the medication user interface 2200, the "last updated" filter 2202*a* has been selected. Thus, the data presented in the medication user interface 2200 includes the most recently updated medication information. As illustrated in FIG. 22, record entries 2204*a* and 2204*b* have been populated; although, other record entries may be revealed if the medication user interface 2200 is scrolled down. The record entry 2204*a* was collected on Mar. 29, 2019 at General Medical Health Care and includes a prescription for acetaminophen and a prescription for albuterol. The record entry 2204b was collected on Aug. 15, 2018 and includes a prescription for cetirizine.

Selection of the "A to Z" filter 2202b in the medication user interface 2300 causes the user device 108 to present a medication user interface 2300. FIG. 23 illustrates the medication user interface 2300 for presenting selected health record data on the user device 108 using a personal health ontology (e.g., the personal health ontology 1102), according to at least one example. The medication user interface 2300 is accessible within a health application (e.g., the health application 218) and illustrated on a display of the user device 108, which is an example of a handheld mobile device. It should be understood, however, that, in some examples, the medication user interface 2300 may be accessible within other applications, which may include web applications, and on displays of other user devices.

The medication user interface 2300 includes an alphabetized medication list 2302. The items included in the medication list 2302 represent that actual health record data exists corresponding to the particular item in the medication list 2302. For example, the health application includes health record data for at least four different medication concepts (e.g., acetaminophen, albuterol, cetirizine, and simvastatin). As such, these records are represented in the medication list 2302. The user device 108 may use the personal health ontology to create and present the medication list 2302. If the health record data included additional medications, then scrolling within the medication user interface 2300 may reveal additional records for the additional medications.

Figure 24:
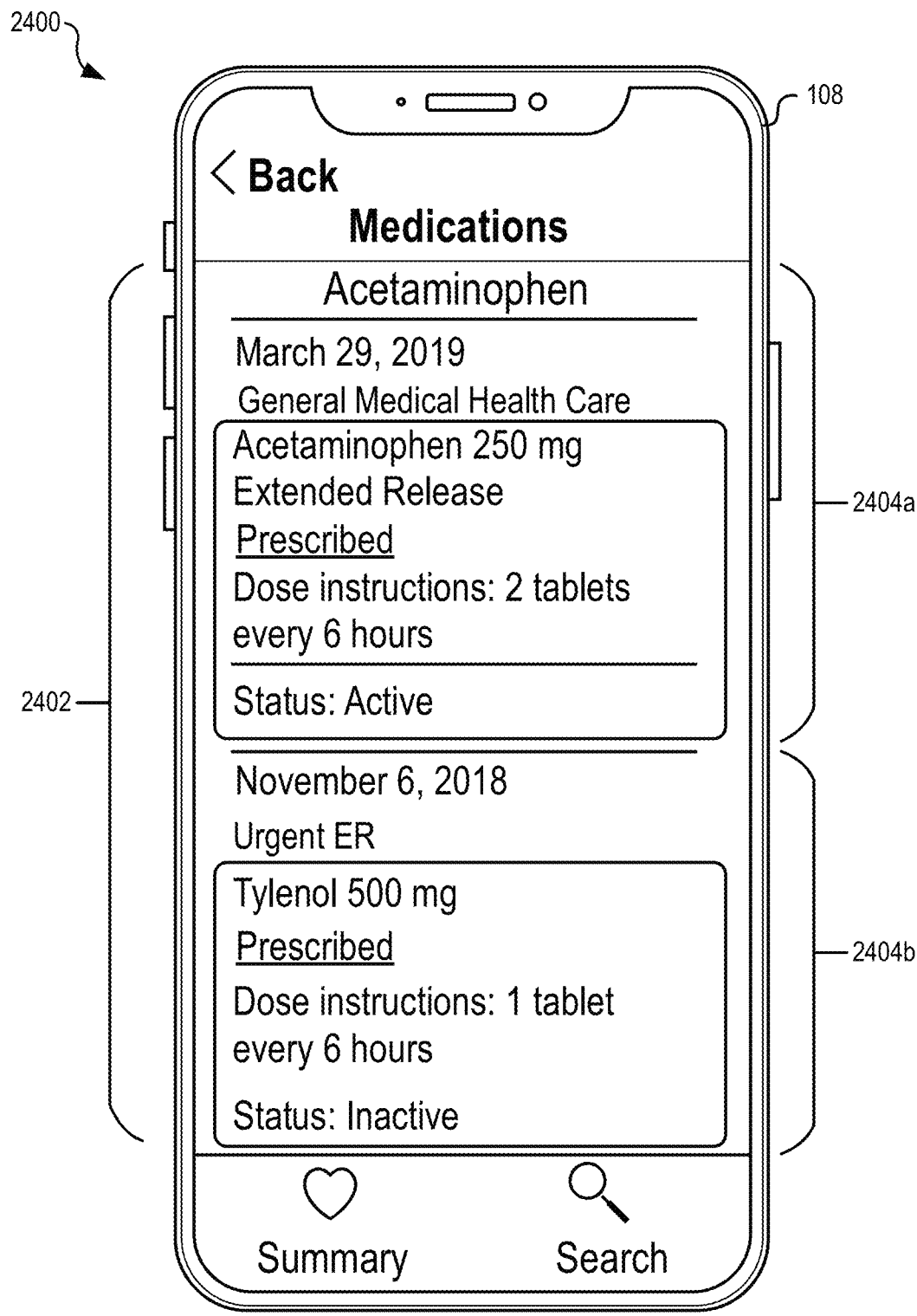
FIG. 24 illustrates a user interface for presenting selected health record data on a user device using a personal health ontology, according to at least one example.

Selection of any one of the items in the medications list 2302 causes the user device 108 to present a detailed user interface specific to the subject matter of the selected item. For example, selection of an item 2302a relating to acetaminophen causes the user device 108 to present a medication user interface 2400 dedicated to acetaminophen, as illustrated in FIG. 24. In some examples, the medication user interface 2400 is referred to as a concept room because it organizes health record data with respect to a particular concept-acetaminophen. Other concepts rooms can be built using the personal health ontology to organize health record data with respect to any other concept such as, for example, conditions, vitals, allergies, procedures, etc.

As introduced previously, FIG. 24 illustrates the medication user interface 2400 for presenting selected health record data on the user device 108 using a personal health ontology (e.g., the personal health ontology 1102), according to at least one example. The medication user interface 2400 is accessible within a health application (e.g., the health application 218) and illustrated on a display of the user device 108, which is an example of a handheld mobile device. It should be understood, however, that, in some examples, the medication user interface 2400 may be accessible within other applications, which may include web applications, and on displays of other user devices.

The medication user interface 2400 includes a record list 2402 including record entries 2404a and 2404b. The record entries 2404 each correspond to a particular event when a prescription of acetaminophen was administered. The record entries 2404 may have been recorded in different instances of a user's health record or within the same instance. For example, the record entry 2404a relates to a Mar. 29, 2019 event at "General Medical Health Care." The record entry 2404a represents a prescription for "acetaminophen 250 mg extended release." The record entry 2404a also identifies whether the prescription is active or inactive and dosage instructions. The record entry 2404b relates to a Nov. 6, 2018 event at "Urgent ER." The record entry 2404b represents a prescription for "Tylenol 500 mg." The record entry 2404b also identifies whether the prescription is active or inactive and dosage instructions. These two record entries 2404 were sourced from different instances of the user's health record and relate to two different medications. Because the curated health ontology, sub-ontology, and personal health ontology are organized by health concepts, the user device 108 is able to identify these seemingly disparate record entries 2404 as being related to the concept of "acetaminophen," and provide for presentation of them together. This may also represent a grouping based on an active ingredient. In some examples, the other medications in the medication list 2302 may be organized and presented similarly. The presentation of the record entries 2404 is also normalized to provide a consistent view of the data.

Turning now to the lab results user interface 2500, FIG. 25 illustrates the lab results user interface 2500 for presenting selected health record data on the user device 108 using a personal health ontology (e.g., the personal health ontology 1102), according to at least one example. The lab results user interface 2500 is accessible within a health application (e.g., the health application 218) and illustrated on a display of the user device 108, which is an example of a handheld mobile device. It should be understood, however, that, in some examples, the lab results user interface 2500 may be accessible within other applications, which may include web applications, and on displays of other user devices.

The lab results user interface 2500 includes a filter section that includes a "last updated" filter 2502a and an "A to Z" filter 2502b. In the lab results user interface 2500, the "last updated" filter 2502a has been selected. Thus, the data presented in the lab results user interface 2500 includes the most recently updated lab results information. As illustrated in FIG. 25, two record entries 2504a and 2504b have been populated; although other record entries may be revealed if the lab results user interface 2500 is scrolled down. The record entry 2504a was collected on Mar. 29, 2019 by General Medical Health Care and includes a cholesterol test and a hemoglobin test. The record entry 2504b was collected on Aug. 15, 2018 by National Health.

Selection of the "A to Z" filter 2502b in the lab results user interface 2500 causes the user device 108 to present a lab results user interface 2600. FIG. 26 illustrates the lab results user interface 2600 for presenting selected health record data on the user device 108 using a personal health ontology (e.g., the personal health ontology 1102), according to at least one example. The lab results user interface 2600 is accessible within a health application (e.g., the health application 218) and illustrated on a display of the user device 108, which is an example of a handheld mobile device. It should be understood, however, that, in some examples, the lab results user interface 2600 may be accessible within other applications, which may include web applications, and on displays of other user devices.

The lab results user interface 2600 includes an alphabetized lab results list 2602. The items included in the lab results list 2602 represent that actual health record data exists corresponding to the particular item in the lab results list 2602. For example, the health application includes health record data for at least five different lab result concepts (e.g., cholesterol, creatine, hemoglobin A1c, LDL cholesterol in blood, and urinalysis). As such, these records are represented in the lab results list 2602. The user device 108 may use the personal health ontology to create and present the lab results list 2602. If the health record data included additional lab results, then scrolling within the lab results user interface 2600 may reveal additional records for the additional lab results.

Selection of any one of the items in the lab results list 2602 causes the user device 108 to present a detailed user interface specific to the subject matter of the selected item. For example, selection of an item 2602a relating to the lab test "hemoglobin A1c" causes the user device 108 to present a lab results user interface 2700, illustrated in FIG. 27, dedicated to this lab test and results from this same or similar test taken at different times. In some examples, the lab results user interface 2700 is referred to as a concept room because it organizes health record data with respect to a particular concept-lab results for "hemoglobin A1c" test. Other concepts rooms can be built using the personal health ontology to organize health record data with respect to any other concept such as, for example, conditions, vitals, allergies, procedures, etc.

Figure 27:
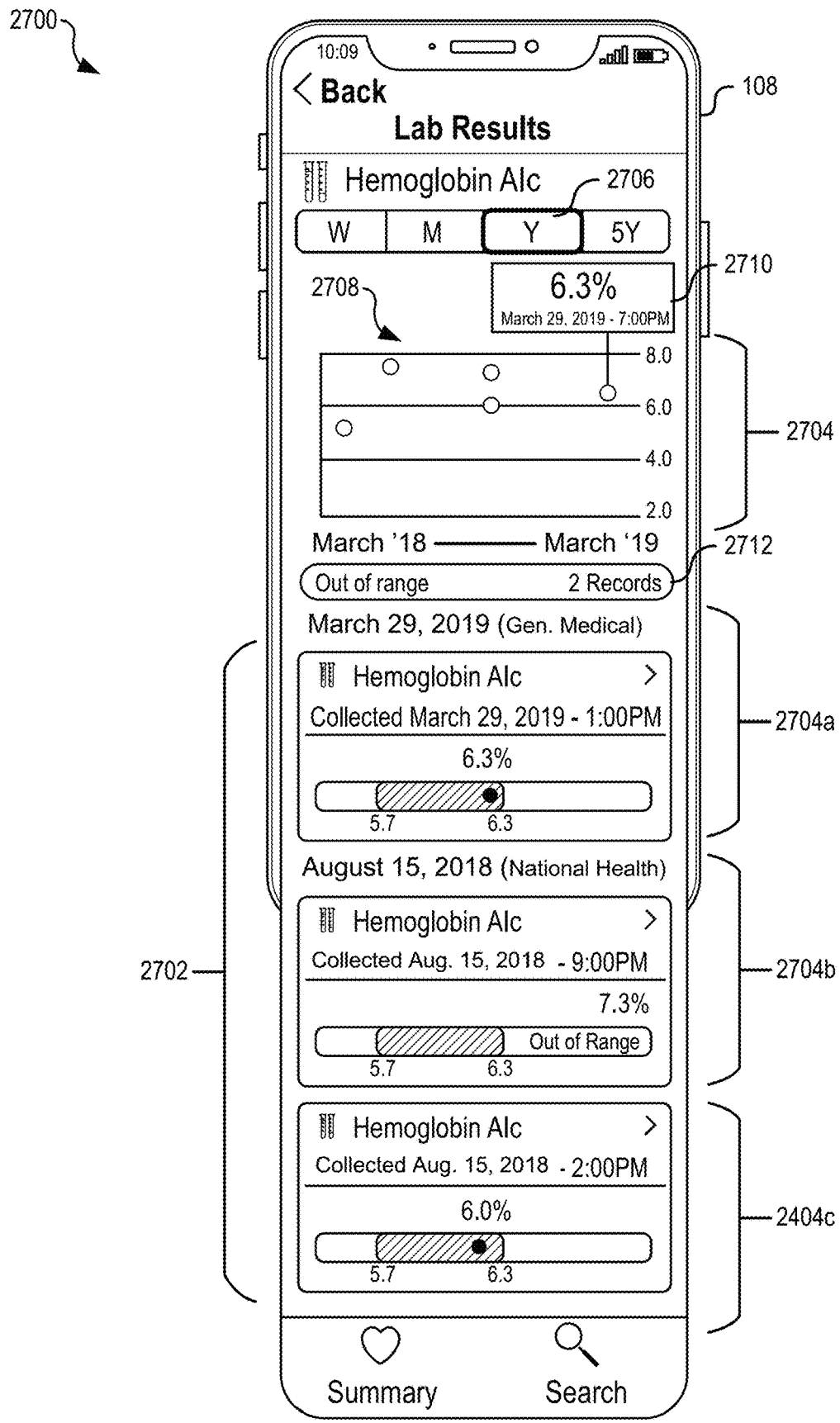
FIG. 27 illustrates a user interface for presenting selected health record data on a user device using a personal health ontology, according to at least one example.

As introduced previously, FIG. 27 illustrates the lab results user interface 2700 for presenting selected health record data on the user device 108 using a personal health ontology (e.g., the personal health ontology 1102), according to at least one example. The lab results user interface 2700 is accessible within a health application (e.g., the health application 218) and illustrated on a display of the user device 108, which is an example of a handheld mobile device. It should be understood, however, that, in some examples, the lab results user interface 2700 may be accessible within other applications, which may include web applications, and on displays of other user devices.

The lab results user interface 2700 includes a record list 2702 including record entries 2704a-2704c. The record entries 2704 each correspond to a particular event when the lab test for Hemoglobin A1c was collected. The record entries 2704 may have been recorded in different instances of a user's health record or within the same instance. For example, the record entry 2704a was collected Mar. 29, 2019 at 1:00 PM. The record entry 2704a includes a graph to show the data point with respect to a normal range. The record entries 2704b and 2704c were collected on Jun. 10, 2019 respectively at 9:00 PM and 2:00 PM. The record entries 2704b and 2704c include graphs to show the data points with respect to a normal range. These three record entries 2704 were sourced from different instances of the user's health record and relate to three different lab tests administered to the user. Because the curated health ontology, sub-ontology, and personal health ontology are organized by health concepts, the user device 108 is able to identify these record entries 2704 as being related to the concept of a "hemoglobin A1c" test, and provide for presentation of them together. In some examples, the other lab results in the record list 2702 may be organized and presented similarly. The presentation of the record entries 2704 is also normalized to provide a consistent view of the data.

The lab results user interface 2700 also includes a filter section that includes a week filter (W), a month filter (M), a year filter (Y) 2706, and a five year filter (5Y). In the illustrated example, the year filter 2706 is selected. The record list 2702 includes the record entries 2704 collected within the last year. Similarly, the lab results user interface 2700 also includes a graph 2708 (e.g., a chart that shows results of the lab tests) that includes data points corresponding to record entries 2704 of the record list 2702. The data points in the graph 2708 may be sourced from multiple instances of the user's health record, administered on different days and times, and administered by different organizations. The user device 108 uses the personal health ontology to organize the data for presentation in the graph 2708.

Selection of any one of the data points may present a summary overlay 2710 that shows a few details about the data point and the test that was administered to obtain the data point. The lab results user interface 2700 also includes an out of range filter 2712. The out of range filter 2712 identifies how many of the record entries 2704 are out of normal range. Selection of the out of range filter 2712 may cause the user device 108 to highlight the two records that are out of range. In some examples, this may include graphically emphasizing the two records, removing or graying out the in range records, or using any other suitable technique to highlight the two records. FIGS. 28 and 29 illustrate an example of graphically highlighting certain records.

Returning now to FIG. 26, selection of any one of the items in the lab results list 2602 causes the user device 108 to present a detailed user interface specific to the subject matter of the selected item. For example, selection of an item 2602b relating to the lab test "LDL cholesterol in blood" causes the user device 108 to present a lab results user interface 2800, as illustrated in FIG. 28, dedicated to this lab test and results from this same or similar test taken at different times. In some examples, the lab results user interface 2800 is referred to as a concept room because it organizes health record data with respect to a particular concept-lab results for "LDL cholesterol in blood" test. Other concepts rooms can be built using the personal health ontology to organize health record data with respect to any other concept such as, for example, conditions, vitals, allergies, procedures, etc.

As introduced previously, FIG. 28 illustrates the lab results user interface 2800 for presenting selected health record data on the user device 108 using a personal health ontology (e.g., the personal health ontology 1102), according to at least one example. The lab results user interface 2800 is accessible within a health application (e.g., the health application 218) and illustrated on a display of the user device 108, which is an example of a handheld mobile device. It should be understood, however, that, in some examples, the lab results user interface 2800 may be accessible within other applications, which may include web applications, and on displays of other user devices.

The lab results user interface 2800 includes a filter section that includes a week filter (W), a month filter (M), a year filter (Y), and a five year filter (5Y) 2802. In the illustrated example, the five year filter 2802 is selected.

The lab results user interface 2800 also includes a graph 2804 that includes seven data points 2805 that correspond to a total of seven records as represented by a record quantity indicator 2806. Thus, seven records representing by the seven data points have been collected over the last five years. As described elsewhere herein, the seven records may have been sourced from different instances of the user's health record and may relate to seven different lab tests administered to the user. Because the curated health ontology, sub-ontology, and personal health ontology are organized by health concepts, the user device 108 is able to identify the seven records as being related to the concept of a "LDL cholesterol in blood" test, and provide for presentation of them together.

The lab results user interface 2800 also includes a filter section 2808. The filter section 2808 includes one or more filters 2810a and 2810b that have been generated based on the health record data and the personal health ontology. The filters 2810, in this example, may be referred to as series filters because they are used to filter series of data presented in the graph 2804 (e.g., the data points 2805). In this example, of the seven records, three were collected using a first technique (the filter 2810a) and are represented by the data points 2805a and four were collected using a second technique (the filter 2810b) and are represented by the data points 2805b. In the lab results user interface 2800 neither of the filters 2810 have been applied, but are instead presented as an option for user selection. The filters 2810 may be helpful to highlight when graphed values are within normal range based on different scales. For example, the LDL cholesterol in blood test when administered using the first technique may result in a value that appears low when compared graphically to the values obtained using the second technique. A user who is not trained and/or does not understand these differences, could misinterpret the results, which could result in confusion. The techniques described herein ameliorate the potential for confusion by identifying when two tests are obtained using different techniques, generating filters 2810 relating to these techniques, and presenting user interface elements (e.g., the filters 2810) that can be used to highlight these differences for the user.

To apply one of the filters 2810, the user simply selects one of the filters 2180. Selection of the filter 2810a causes the user device 108 to apply a filter to the data points 2805 in the graph 2804 to highlight the three data points 2805a corresponding to the three records obtained using the first technique. In particular, this selection causes a lab results user interface 2900 to be presented, as illustrated in FIG. 29. In some examples, the range (e.g., 25-120 mg/dL) in the lab results user interface 2900 is updated based on the selection of the filter 2810a. For example, the range may be adjusted to correspond to an appropriate range for technique 1. The range in the lab results user interface 2800 may represent a range for technique 2, a range for technique 2, or a range that is based on both techniques (e.g., a range that includes an uppermost value for the two techniques and a lowermost value for the two techniques).

As introduced previously, FIG. 29 illustrates the lab results user interface 2900 for presenting selected health record data on the user device 108 using a personal health ontology (e.g., the personal health ontology 1102), according to at least one example. The lab results user interface 2900 is accessible within a health application (e.g., the health application 218) and illustrated on a display of the user device 108, which is an example of a handheld mobile device. It should be understood, however, that, in some examples, the lab results user interface 2900 may be accessible within other applications, which may include web applications, and on displays of other user devices.

The lab results user interface 2900 is very similar to the lab results user interface 2800, except that the data points 2805a have been highlighted as a result of the filter 2810a being selected by the user. The data points 2805a, in this example, are highlighted graphically by enlarging the data points 2805a as compared to the data points 2805b. In some examples, other approaches for highlighting may also be used (e.g., changing colors, flashing elements, contrasting colors, removal of the data points 2805b, graying out of the data points 2805b, and any other suitable approach).

Figure 30:
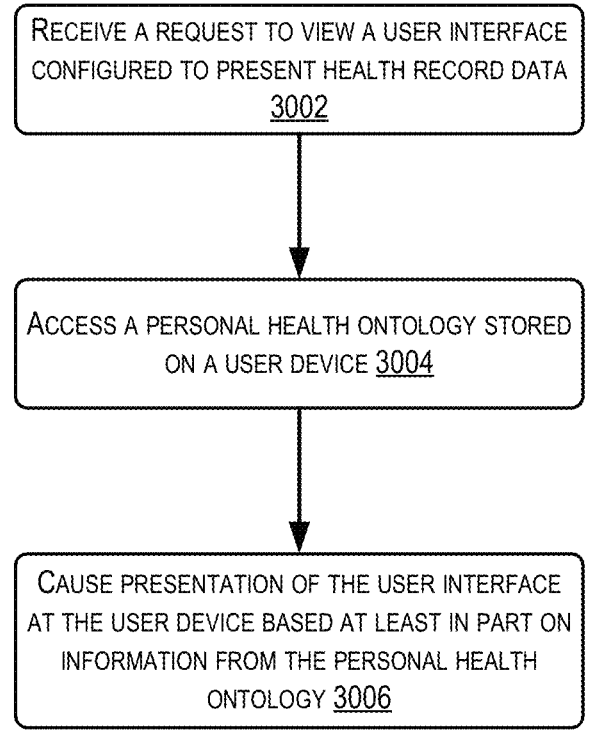
FIG. 30 illustrates a flow chart showing an example process for presenting selected health record data on a user device using a personal health ontology, according to at least one example.

FIG. 30 illustrates a flow chart showing an example process 3000 for presenting selected health record data on a user device using a personal health ontology, according to at least one example. The process 3000 may be performed by the grouping user interface generation engine 1008 (FIG. 10) of the user device 108 (FIG. 1).

The process 3000 begins at 3002 by the grouping user interface generation engine 1008 receiving a request to view a user interface configured to present health record data. In some examples, the request may be received at a user device that includes the grouping user interface generation engine 1008. The health record data may be stored on the user device and associated with a user profile corresponding to the user device.

At 3004, the process 3000 includes the grouping user interface generation engine 1008 accessing a personal health ontology stored on the user device. The personal health ontology may represent associations between health record codes of the health record data and concept nodes of a curated health sub-ontology stored on the user device. The personal health ontology may be specific to the user profile.

At 3006, the process 3000 includes the grouping user interface generation engine 1008 causing presentation of the user interface at the user device based at least in part on information from the personal health ontology. In some examples, the user interface may include a plurality of category user interface elements that represent a plurality of health record categories of the health record categories. The plurality of category user interface elements may correspond to the items in the health record section 1608 or other suitable portions of the user interfaces described herein.

In some examples, the process 3000 may further include determining individual health record categories for the health record codes based at least in part on the health record data, and storing associations between the health record categories and the health record codes in the personal health ontology.

In some examples, the process 3000 may further include using the personal health ontology to group items of the health record data with respect to the plurality of category user interface elements.

In some examples, the process 3000 may further include receiving a selection of a category user interface element of the plurality of user interface elements, determining a set of items from the health record data based at least in part on a health record category associated with the first category user interface element and the personal health ontology, and causing presentation of a category user interface that represents the set of items. In some examples, the category user interface represents the set of items in at least one of a time-sorted list including the set of items or an alphabetized list including the set of items. In some examples, the health record category is a medication category and the set of items includes a set of medications from the health record data. In some examples, the set of medications may include medications identified from different instances of a personal electronic health record and prescribed by different providers at different times. In some examples, the process 3000 may further include grouping the set of medications based at least in part on an active ingredient of each of medication of the set of medications.

In some examples, the health record category may be a lab category and the set of items may include a set of lab results from the health record data. In some examples, the set of lab results may include findings identified from different instances of a personal electronic health record providers at different times. In some examples, the process 3000 may further include grouping the set of lab results based at least in part on at least one of a component of a respective lab result or a specimen of the respective lab result.

In some examples, the health record category may be an immunization category and the set of items may include a set of immunization records from the health record data. In some examples, the process 3000 may further include grouping the set of immunization records based at least in part on a disease pathogen of a respective immunization record.

In some examples, the health record category may be a vitals category and the set of items may include a set of vital records from the health record data. In some examples, the process 3000 may further include grouping the set of immunization records based at least in part on blood pressure, body height, body length, body temperature, body mass index, heart rate, head circumference, oxygen saturation, respiratory rate, and weight.

In some examples, the plurality of health record categories may include an allergy category, a vitals category, a conditions category, an immunization category, a lab results category, a medications category, and a procedures category.

In some examples, the health record data may include first health record data from a first health institution and second health record data from a second health institution. In some examples, the first health record data may include a first instance of a personal electronic health record of a user associated with the user profile, and the second health record data may include a second instance of the personal electronic health record of the user.

Figure 31:
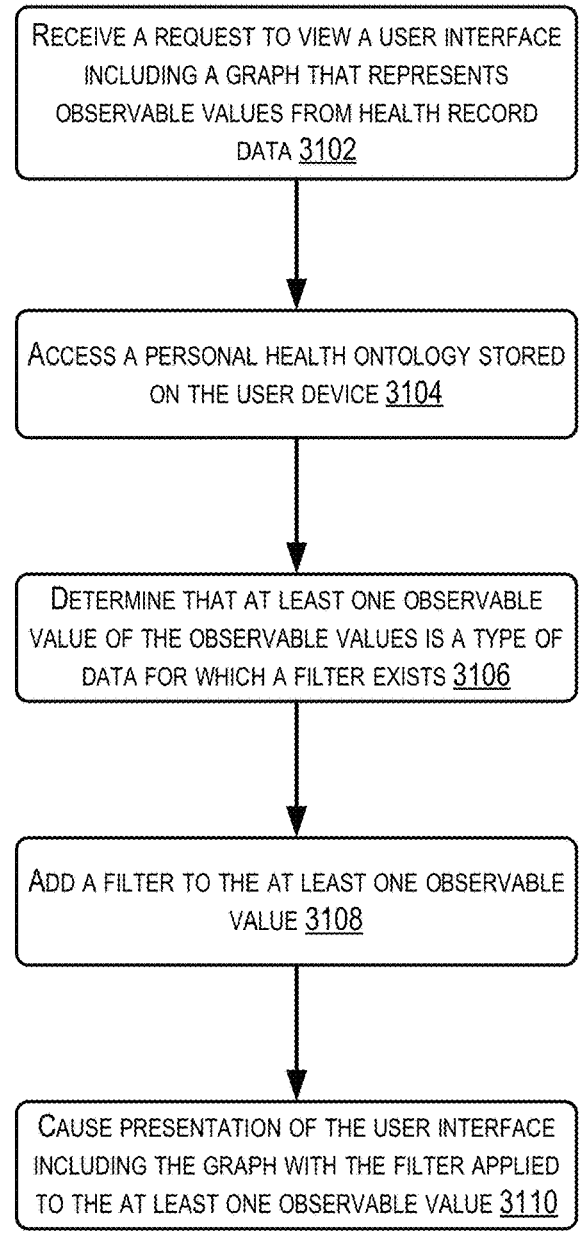
FIG. 31 illustrates a flow chart showing an example process for presenting selected health record data on a user device using a personal health ontology, according to at least one example.

FIG. 31 illustrates a flow chart showing an example process 3100 for presenting selected health record data on a user device using a personal health ontology, according to at least one example. The process 3100 may be performed by the graphing user interface generation engine 1010 (FIG. 10) of the user device 108 (FIG. 1).

The process 3100 begins at 3102 by the graphing user interface generation engine 1010 receiving a request to view a user interface including a graph that represents observable values from health record data. The request may be received at the user device. The health record data may be stored on the user device. The health record data may be associated with a user profile corresponding to the user device. In some examples, the observable values may include clinical lab values or vital sign values. In some examples, the at least one observable value was obtained from a user by a health professional using a first technique, and at least one other observable value of the observable values was obtained by a health professional from the user using a second technique. The user may be associated with the user profile.

At 3104, the process 3100 includes the graphing user interface generation engine 1010 accessing a personal health ontology stored on the user device. The personal health ontology may represent associations between the observable values and one or more concept nodes of a curated health sub-ontology stored on the user device. In some examples, the personal health ontology may be specific to the user profile. In some examples, the personal health ontology may uniquely represent the health record data.

At 3106, the process 3100 includes the graphing user interface generation engine 1010 determining that at least one observable value of the observable values is of a type of data for which a filter exists. This may performed by at least accessing the personal health ontology. For example, the personal health ontology may include an entry that indicates which types of data may have associated filters.

At 3108, the process 3100 includes the graphing user interface generation engine 1010 adding a filter to the at least one observable value. This may cause an update to the user interface.

At 3110, the process 3100 includes the graphing user interface generation engine 1010 causing presentation of the user interface including the graph with the filter applied to the at least one observable value.

In some examples, the health record data may include first health record data from a first health institution, and second health record data from a second health institution. In some examples, the first health record data may include the at least one observable value, and the second health record data may include at least one other observable value of the observable values. In some examples, the first health record data may include a first instance of a personal electronic health record of a user associated with the user profile, and the second health record data may include a second instance of the personal electronic health record of the user.

In some examples, a particular association between a particular concept node of the one or more concept nodes may define that the at least one observable value is the type of data for which the filter exists. In some examples, the user interface may include a graph region including the graph and a filter region including a user interface element that represents the filter. In some examples, the filter may include a graphical overlay to highlight differences between the at least one observable value and at least one other observable value of the observable values.

In some examples, the process 3100 may further include, prior to accessing the personal health ontology, downloading the curated health sub-ontology from a server device that hosts a curated health ontology. In some examples, the curated health sub-ontology may include an instance of the curated health ontology. The curated health ontology may include a first quantity of concept nodes that is greater than a second quantity of concept nodes of the curated health sub-ontology. In some examples, the curated health ontology may be based at least in part on a standard health coding ontology and at least one standard health coding terminology. The standard health coding ontology may be based at least in part on the SNOMED® Clinical Terms (CT) standard. The standard health coding terminology may include at least one of a clinical drug coding standard, a clinical lab results coding standard, a health record transportation coding standard, a vaccine coding standard, or a clinical imaging coding standard. In some examples, the curated health sub-ontology and the personal health ontology may be stored in a database on the user device In some examples, at least one concept node of the one or more concept nodes may include a sub-concept node connected to the at least one concept node via a link. The link may semantically represent the relationship between the at least one concept node and the sub-concept node.

Figure 32:
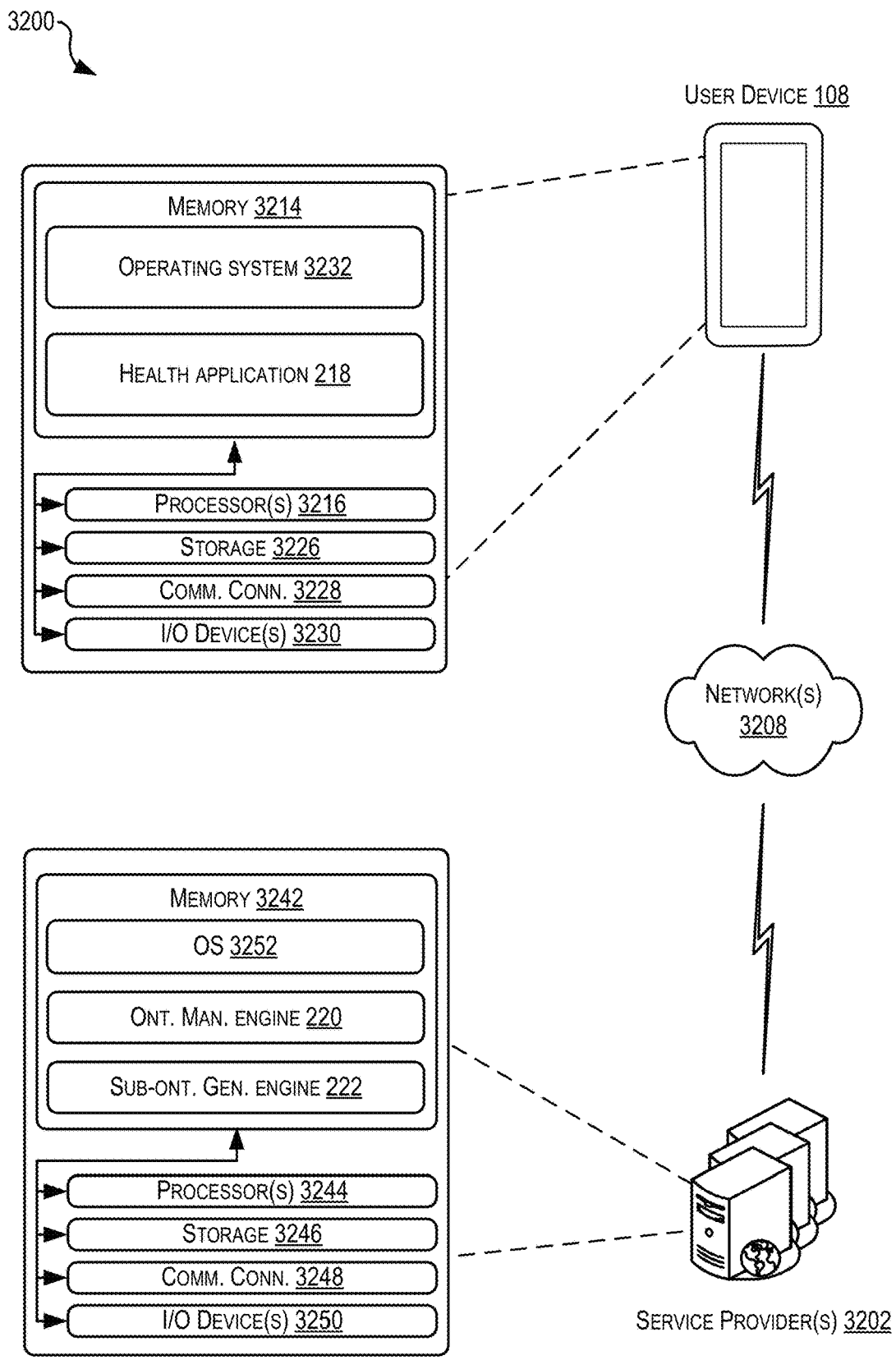
FIG. 32 illustrates a simplified block diagram depicting an example architecture for implementing the techniques described herein, according to at least one example.

FIG. 32 illustrates an example architecture or environment 3200 configured to implement techniques described herein, according to at least one example. In some examples, the example architecture 3200 may further be configured to enable the user device 108, service provider computers 3202 to share information. The service provider computers 3202 are examples of the ontology management system 104. In some examples, the business subscription system 206 and/or the provider Web system 204 may take a similar form as the service provider computers 3202. In some examples, the devices may be connected via one or more networks 3208 (e.g., via Bluetooth, WiFi, the Internet, or the like). In some examples, the service provider computers 3202 may be configured to implement at least some of the techniques described herein with reference to the user device 108.

In some examples, the networks 3208 may include any one or a combination of many different types of networks, such as cable networks, the Internet, wireless networks, cellular networks, satellite networks, other private and/or public networks, or any combination thereof. While the illustrated example represents the user device 108 accessing the service provider computers 3202 via the networks 3208, the described techniques may equally apply in instances where the user device 108 interacts with the service provider computers 3202 over a landline phone, via a kiosk, or in any other manner. It is also noted that the described techniques may apply in other client/server arrangements (e.g., set-top boxes, etc.), as well as in non-client/server arrangements (e.g., locally stored applications, peer to peer configurations, etc.).

As noted above, the user device 108 may be any type of computing device such as, but not limited to, a mobile phone, a smartphone, a personal digital assistant (PDA), a laptop computer, a desktop computer, a thin-client device, a tablet computer, a wearable device, or the like. In some examples, the user device 108 may be in communication with the service provider computers 3202 via the network 3208, or via other network connections.

In one illustrative configuration, the user device 108 may include at least one memory 3214 and one or more processing units (or processor(s)) 3216. The processor(s) 3216 may be implemented as appropriate in hardware, computer-executable instructions, firmware, or combinations thereof. Computer-executable instruction or firmware implementations of the processor(s) 3216 may include computer-executable or machine-executable instructions written in any suitable programming language to perform the various functions described. The user device 108 may also include geo-location devices (e.g., a global positioning system (GPS) device or the like) for providing and/or recording geographic location information associated with the user device 108.

The memory 3214 may store program instructions that are loadable and executable on the processor(s) 3216, as well as data generated during the execution of these programs. Depending on the configuration and type of the user device 108, the memory 3214 may be volatile (such as random access memory (RAM)) and/or non-volatile (such as read-only memory (ROM), flash memory, etc.). The user device 108 may also include additional removable storage and/or non-removable storage 3226 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 3214 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 3214 and the additional storage 3226, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 3214 and the additional storage 3226 are both examples of non-transitory computer storage media. Additional types of computer storage media that may be present in the user device 108 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 108. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 108 may also contain communications connection(s) 3228 that allow the user device 108 to communicate with a data store, another computing device or server, user terminals, and/or other devices via the network 3208. The user device 108 may also include I/O device(s) 3230, such as a keyboard, a mouse, a pen, a voice input device, a touch input device, a display, speakers, a printer, etc.

Turning to the contents of the memory 3214 in more detail, the memory 3214 may include an operating system 3232 and/or one or more application programs or services for implementing the features disclosed herein such as the health application 218. In some examples, the server provider computer 3202 may also include a health application to perform similar techniques as described with reference to the user device 108. Similarly, at least some techniques described with reference to the server provider computer 3202 may be performed by the user device 108.

The service provider computers 3202 may also be any type of computing device such as, but not limited to, a mobile phone, a smartphone, a PDA, a laptop computer, a desktop computer, a thin-client device, a tablet computer, a wearable device, a server computer, a virtual machine instance, etc. In some examples, the service provider computers 3202 may be in communication with the user device 108 via the network 3208, or via other network connections.

In one illustrative configuration, the service provider computers 3202 may include at least one memory 3242 and one or more processing units (or processor(s)) 3244. The processor(s) 3244 may be implemented as appropriate in hardware, computer-executable instructions, firmware, or combinations thereof. Computer-executable instruction or firmware implementations of the processor(s) 3244 may include computer-executable or machine-executable instructions written in any suitable programming language to perform the various functions described.

The memory 3242 may store program instructions that are loadable and executable on the processor(s) 3244, as well as data generated during the execution of these programs. Depending on the configuration and type of service provider computer 3202, the memory 3242 may be volatile (such as RAM) and/or non-volatile (such as ROM, flash memory, etc.). The service provider computer 3202 may also include additional removable storage and/or non-removable storage 3246 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 3242 may include multiple different types of memory, such as SRAM, DRAM, or ROM. While the volatile memory described herein may be referred to as RAM, any volatile memory that would not maintain data stored therein once unplugged from a host and/or power would be appropriate. The memory 3242 and the additional storage 3246, both removable and non-removable, are both additional examples of non-transitory computer-readable storage media.

The service provider computer 3202 may also contain communications connection(s) 3248 that allow the service provider computer 3202 to communicate with a data store, another computing device or server, user terminals and/or other devices via the network 3208. The service provider computer 3202 may also include I/O device(s) 3250, such as a keyboard, a mouse, a pen, a voice input device, a touch input device, a display, speakers, a printer, etc.

Turning to the contents of the memory 3242 in more detail, the memory 3242 may include an operating system 3252 and/or one or more application programs or services for implementing the features disclosed herein including the ontology management engine 220 and the sub-ontology generation engine 222.

The various examples further can be implemented in a wide variety of operating environments, which in some cases can include one or more user computers, computing devices or processing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as RAM or ROM, as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets) or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

As described above, one aspect of the present technology is the gathering and use of data available from various sources to provide a comprehensive and complete window to a user's personal health record. The present disclosure contemplates that in some instances, this gathered data may include personally identifiable information (PII) data that uniquely identifies or can be used to contact or locate a specific person. Such personal information data can include demographic data, location-based data, telephone numbers, email addresses, Twitter ID's, home addresses, data or records relating to a user's health or level of fitness (e.g., vital sign measurements, medication information, exercise information), date of birth, health record data, or any other identifying or personal or health information.

The present disclosure recognizes that the use of such personal information data, in the present technology, can be used to the benefit of users. For example, the personal information data can be used to provide enhancements to a user's personal health record. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services or other services relating to health record management, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. A computer-implemented method, comprising:
receiving, at a user device, a request to view a user interface comprising a graph that represents observable values from health record data stored on the user device, the health record data associated with a user profile corresponding to the user device;
accessing a personal health ontology stored on the user device, the personal health ontology representing associations between the observable values and one or more concept nodes of a curated health sub-ontology stored on the user device;
determining that at least one observable value of the observable values is of a type of data for which a filter exists by at least accessing the personal health ontology;
adding a filter to the at least one observable value; and
causing presentation, at the user device, of the user interface comprising the graph with the filter applied to the at least one observable value.

2. The computer-implemented method of claim 1, wherein the personal health ontology is specific to the user profile.

3. The computer-implemented method of claim 1, wherein the personal health ontology uniquely represents the health record data.

4. The computer-implemented method of claim 1, wherein the health record data comprises first health record data from a first health institution, and second health record data from a second health institution.

5. The computer-implemented method of claim 4, wherein the first health record data comprises the at least one observable value, and the second health record data comprises at least one other observable value of the observable values.

6. The computer-implemented method of claim 5, wherein the first health record data comprises a first instance of a personal electronic health record of a user associated with the user profile, and the second health record data comprises a second instance of the personal electronic health record of the user.

7. The computer-implemented method of claim 1, wherein the observable values comprise clinical lab values or vital sign values.

8. A system, comprising:
a memory configured to store computer-executable instructions; and
one or more processors in communication with the memory and configured to access the memory and execute the computer-executable instructions to at least:
receive, at a user device, a request to view a user interface comprising a graph that represents observable values from health record data stored on the user device, the health record data associated with a user profile corresponding to the user device;
access a personal health ontology stored on the user device, the personal health ontology representing associations between the observable values and one or more concept nodes of a curated health sub-ontology stored on the user device;
determine that at least one observable value of the observable values is of a type of data for which a filter exists by at least accessing the personal health ontology;
add a filter to the at least one observable value; and
cause presentation, at the user device, of the user interface comprising the graph with the filter applied to the at least one observable value.

9. The system of claim 8, wherein the at least one observable value was obtained from a user by a health professional using a first technique, at least one other observable value of the observable values was obtained by a health professional from the user using a second technique, and the user is associated with the user profile.

10. The system of claim 8, wherein a particular association between a particular concept node of the one or more concept nodes defines that the at least one observable value is the type of data for which the filter exists.

11. The system of claim 8, wherein the user interface comprises a graph region comprising the graph and a filter region comprising a user interface element that represents the filter.

12. The system of claim 8, wherein the filter comprises a graphical overlay to highlight differences between the at least one observable value and at least one other observable value of the observable values.

13. The system of claim 8, wherein the one or more processors are configured to access the memory and execute additional computer-executable instructions to at least, prior to accessing the personal health ontology, download the curated health sub-ontology from a server device that hosts a curated health ontology.

14. The system of claim 13, wherein the curated health sub-ontology comprises an instance of the curated health ontology, the curated health ontology comprising a first quantity of concept nodes that is greater than a second quantity of concept nodes of the curated health sub-ontology.

15. One or more non-transitory computer-readable storage devices comprising computer-executable instructions that, when executed by one or more processors of a computer system, cause the computer system to perform operations comprising:
receiving, at a user device, a request to view a user interface comprising a graph that represents observable values from health record data stored on the user device, the health record data associated with a user profile corresponding to the user device;
accessing a personal health ontology stored on the user device, the personal health ontology representing associations between the observable values and one or more concept nodes of a curated health sub-ontology stored on the user device;

determining that at least one observable value of the observable values is of a type of data for which a filter exists by at least accessing the personal health ontology;

adding a filter to the at least one observable value; and causing presentation, at the user device, of the user interface comprising the graph with the filter applied to the at least one observable value.

16. The one or more non-transitory computer-readable storage devices of claim 15, wherein the personal health ontology is based at least in part on a standard health coding ontology and at least one standard health coding terminology.

17. The one or more non-transitory computer-readable storage devices of claim 16, wherein the standard health coding ontology is based at least in part on the SNOMED Clinical Terms (CT) standard.

18. The one or more non-transitory computer-readable storage devices of claim 17, wherein the standard health coding terminology comprises at least one of a clinical drug coding standard, a clinical lab results coding standard, a health record transportation coding standard, a vaccine coding standard, or a clinical imaging coding standard.

19. The one or more non-transitory computer-readable storage devices of claim 15, wherein at least one concept node of the one or more concept nodes comprises a sub-concept node connected to the at least one concept node via a link, the link semantically representing the relationship between the at least one concept node and the sub-concept node.

20. The one or more non-transitory computer-readable storage devices of claim 15, wherein the curated health sub-ontology and the personal health ontology are stored in a database on the user device.

* * * * *